(12) United States Patent
Faulk

(10) Patent No.: US 7,417,023 B2
(45) Date of Patent: Aug. 26, 2008

(54) TARGETED DELIVERY OF BIOAFFECTING COMPOUNDS FOR THE TREATMENT OF CANCER

(75) Inventor: W. Page Faulk, Indianapolis, IN (US)

(73) Assignee: Faulk Pharmaceuticals, Inc., St. Simons Island, GA (US)

( * ) Notice: Subject to any disclaimer, the term of this patent is extended or adjusted under 35 U.S.C. 154(b) by 0 days.

(21) Appl. No.: 11/212,664

(22) Filed: Aug. 29, 2005

(65) Prior Publication Data

US 2006/0019876 A1   Jan. 26, 2006

Related U.S. Application Data

(62) Division of application No. 10/477,998, filed as application No. PCT/US02/11890 on May 15, 2002, now Pat. No. 7,001,991.

(60) Provisional application No. 60/291,016, filed on May 16, 2001, provisional application No. 60/291,015, filed on May 16, 2001, provisional application No. 60/290,681, filed on May 15, 2001.

(51) Int. Cl.
| A61K 31/16 | (2006.01) |
| A61K 31/4985 | (2006.01) |
| A61K 38/17 | (2006.01) |
| A61K 38/31 | (2006.01) |
| A61K 38/40 | (2006.01) |

(52) U.S. Cl. .................. 514/6; 514/8; 514/14; 514/21; 514/249; 514/616

(58) Field of Classification Search ....................... None
See application file for complete search history.

(56) References Cited

U.S. PATENT DOCUMENTS

| 4,886,780 | A | | 12/1989 | Faulk | |
| 4,895,714 | A | | 1/1990 | Faulk | |
| 5,000,935 | A | | 3/1991 | Faulk | |
| 5,108,987 | A | | 4/1992 | Faulk | |
| 5,208,323 | A | * | 5/1993 | Page et al. | 530/391.9 |
| 5,238,940 | A | | 8/1993 | Liu et al. | |
| 5,688,488 | A | * | 11/1997 | Low et al. | 424/1.69 |
| 5,744,499 | A | * | 4/1998 | Quash et al. | 514/639 |
| 5,906,977 | A | * | 5/1999 | Sinn et al. | 514/12 |
| 6,133,437 | A | * | 10/2000 | Korneluk et al. | 536/24.5 |
| 6,548,531 | B2 | * | 4/2003 | Breimer et al. | 514/414 |
| 7,001,991 | B2 | * | 2/2006 | Faulk | 530/380 |
| 7,101,842 | B2 | | 9/2006 | Faulk | |
| 2002/0137901 | A1 | * | 9/2002 | Cavanaugh | 530/400 |
| 2004/0028686 | A1 | | 2/2004 | Faulk | |
| 2004/0152071 | A1 | | 8/2004 | Faulk | |
| 2004/0167061 | A1 | | 8/2004 | Faulk | |
| 2004/0204339 | A1 | * | 10/2004 | DiMartino | 514/2 |
| 2004/0220086 | A1 | | 11/2004 | Faulk | |

FOREIGN PATENT DOCUMENTS

| WO | WO 00/66090 A1 | 11/2000 |
| WO | WO 02/00170 A2 | 1/2002 |
| WO | WO 02/091991 A2 | 11/2002 |
| WO | WO 02/091992 A1 | 11/2002 |
| WO | WO 02/092116 A1 | 11/2002 |
| WO | WO 03/004559 A1 | 1/2003 |
| WO | WO 03/032899 A2 | 4/2003 |

OTHER PUBLICATIONS

Leamon et al. Selective Targeting of Malignant Cells with Cytotoxin-Folate Conjugates. Journal of Drug Targeting. 1994, vol. 2, pp. 101-112.*

Mathias et al. Tumor-Selective Radiopharmaceutical Targeting via Receptor-Mediated Endocytosis of Gallium-67- Deferoxamine-Folate. Journal of Nuclear Medicine. Jun. 1996, vol. 37, No. 6, pp. 1003-1008.*

Wang et al. Synthesis, Purification, and Tumor Cell Uptake of 67Ga-Deferoxamine-Folate . . . Bioconjugate Chemistry. 1996, vol. 7, No. 1, pp. 56-62.*

Database CA 'Online!, Chemical Abstracts Service, "Trials of molecular targeting to overcome multidrug resistance". Database accession No. 2000:151715, abstract. (2000).

Berczi et al., "Adriamycin conjugates of human transferrin bind transferrin receptors and kill K562 and HL60 cells", Archives of Biochemistry and Biophysics, 300(1), 356-63 Coden: ABBIA4: ISSN: 003-9861, 1993.

Hoshino et al., "Receptor-binding, in vitro cytotoxicity, and in vivo distribution of transferrin-bound cis-platinum (II) of differing molar ratios", Journal of Controlled Release, vol. 37, No. 1, Nov. 1995, pp. 75-81.

Faulk WO and Johnson PM. Immunological studies of human placentae. Identification and distribution of proteins in mature chorionic villi. Clin Exp Immunol 1977; 27: 365-375.

(Continued)

Primary Examiner—Jeffrey E Russel
(74) Attorney, Agent, or Firm—Rothwell, Figg, Ernst & Manbeck, P.C.

(57) ABSTRACT

A homogeneous conjugate for targeting and treating diseased cells wherein the conjugate comprises an anti-cancer drug and a targeting protein, wherein said anti-cancer drug is selected from the group consisting of heat sensitizers, photosensitizers and apoptosis inducing compounds, a method for making such a conjugate, and methods for using the conjugate. The targeting protein is preferably transferrin.

4 Claims, No Drawings

OTHER PUBLICATIONS

Faulk WP, Johnson PM, Dorling J and Temple A. Non-specific factors of resistance in human placentae. Prot Biol Fluids 1976; 24: 139-142.

Johnson PM and Faulk WP. Immunological studies of human placentae: Identification and distribution of proteins in immature chorionic villi. Immunology 1978; 34: 1027-1035.

Faulk WP and Galbraith GMP. Trophoblast transferrin and transferrin receptors in the host-parasite relationship of human pregnancy. Proc R Soc Lond B 1979; 204: 83-97.

Hsi BL, Yeh CJG and Faulk WP. Human amniochorion: Tissue-specific markers, transferrin receptors and histocompatibility antigens. Placenta 1982; 3: 1-12.

Yeh CJG, Hsi BL and Faulk WP. Histocompatibility antigens, transferrin receptors and extra-embryonic markers of human amniotic epithelial cells in vitro. Placenta 1983; 4: 361-368.

Galbraith GMP, Galbraith RM and Faulk WP. Transferrin binding by human lymphoblastoid cell lines and other transformed cells. Cell Immunology 1980; 49: 215-222.

Faulk WP, Hsi BL and Stevens PJ. Transferrin and transferrin receptors in carcinoma of the breast. Lancet 1980; ii: 390-392.

Yeh CGJ, Taylor C and Faulk WP. Trasferrin binding by peripheral blood mononuclear cells in human lymphomas, myelomas and leukemias. Vox Sanguinis 1984; 46: 217-223.

Faulk WP, Harats H and Berczi A. Transferrin receptor growth control in normal and abnormal cells. In: *Oxidoreduction at the Plasma Membrane*. vol. 1. (eds., FL Crane, JD Moore and H Low) CRC Press, Boca Raton, FL, 1990; pp. 205-224.

Yang DC, Wang F, Elliott RL and Head JF. Expression of transferrin receptor and ferritin H-chain mRNA are associated with clinical and histopathological prognostic indicators in breast cancer. Anticancer Res. 2001; 21: 541-549.

Barnett D, Wilson GA, Lawrence AC and Buckley GA. Transferrin receptor expression in the leukaemias and lymphoproliferative disorders. Clin Lab Haematol 1987; 9: 361-70.

Whitney JF, Clark JM, Griffin TW, Gautam S and Leslie KO. Transferrin receptor expression in nonsmall cell lung cancer. Histopathologic and clinical correlates. Cancer 1995; 76: 20-25.

Recht L, Torres CO, Smith TW, Raso V and Griffin TW. Transferrin receptor in normal and neoplastic brain tissue: implications for brain-tumor immunotherapy. J Neurosurg 1990; 72: 941-945.

Sciot R, Paterson AC, van Eyken P, Callea F, Kew MC and Desmet VJ. Transferrin receptor expression in human hepatocellular carcinoma: an immunohistochemical study of 34 cases. Histopathol 1988; 12: 53-63.

Seymour GJ, Walsh MD, Lavin MF, Strutton G and Gardiner RA. Transferrin receptor expression by human bladder transitional cell carcinomas. Urol Res 1987; 15: 341-344.

Lindholm ML, Lindberg LA, Vilja P, Puolakka VM, Nordling S, Schroder T and Schroder J. Expression of the human transferrin receptor in subrenal capsule assay in the mouse. J Surg Oncol 1988; 38: 57-62.

Hereiz HA and Bayoumi FA. Evaluation of diagnosis of ovarian malignancy using immunohistochemical technique. J Egyptian Public Hlth Assoc 1992; 67: 696-707.

Medeiros LJ, Picker LJ, Horning SJ and Warnke RA. Transferrin receptor expression by non-Hodgkin's lymphomas. Correlation with morphologic grade and survival. Cancer 1988; 61: 1844-1851.

Soyer HP, Smolle J, Torne R and Kerl H. Transferrin receptor expression in normal skin and in various cutaneous tumors. J Cutaneous Pathol 1987; 14: 1-5.

Lesley J. Hyman R, Schulte R. and Trotter J. Expression of transferrin receptor on murine hematopoietic progenitors. Cell Immunol 1984; 83: 14-25.

Testa U, Pelosi E and Peschle C. The transferrin receptor. Crit Rev Oncogen 1993; 4: 241-276.

Bothwell TA, Charlton RW, Cook JD and Finch CA. *Iron Metabolism in Man*, Blackwell Scientific, Oxford, 1979.

Ponka P and Lock CN. The transferrin receptor: role in health and disease. Int J Biochem Cell Biol 1999; 31: 1111-1137.

Hamilton TA, Gray PW and Adams DO. Expression of the transferrin receptor on murine peritoneal macrophages is modulated by in vitro treatment with interferon gamma. Cell Immunol 1984; 89: 478-488.

Byrd TF and Horowitz MA. Interferon gamma-activated human monocytes downregulate transferrin receptors and inhibits the intracellular multiplication of *Legionella. pneumophila* by limiting the availability of iron. J Clin Invest 1989; 83: 1457-1465.

Kronke M. Leonard W, Depper JM and Green WC. Sequential expression of genes involved in human T lymphocyte growth and differentiation. J Exp Med 1985; 161: 1593-1598.

Galbraith RM and Galbriath GM. Expression of transferrin receptors on mitogenstimulated human peripheral blood lymphocytes: relation to cellular activation and related metabolic events. Immunology 1983; 133: 703-710.

Neckers LM and Cossman J. Transferrin receptor induction in mitogen-stimulated human T lymphocytes is required for DNA synthesis and cell division and is regulated by interleukin 2, Proc Nat Acad Sci USA 1983; 80: 3494-3498.

Testa U, Kuhn L, Petrini M, Quaranta MT, Pelosi E and Peschle C. Differential regulation of iron regulatory element-binding protein(s) in cell extracts of activated lymphocytes versus monocytes-macrophages. J Biol Chem 1991; 266: 3925-3930.

Seiser C, Texieira S and Knhn LC. Interleukin-2-dependent transcriptional and post-transcriptional regulation of transferrin receptor mRNA. J Biol Chem 1993; 268:13,074-13,080.

Neckers LM, Yenokida G and James SP. The role of the transferrin receptor in human B lymphocyte activation. J Immunol 1984; 133: 2437-2441.

Neckers LM and Trepel JB, Transferrin receptor expression and the control of cell growth. Cancer Invest 1986; 4: 461-470.

Yeh CJG, Papamichail M and Faulk WP. Loss of transferrin receptors following induced differentiation of HL-60 promyelocytic leukemia cells. Exper Cell Res 1982; 138: 429-431.

Barker KA and Newburger PE. Relationship between the cell cycle and the expression c-myc and transferrin receptor genes during induced myeloid differentiation. Exper Cell Res. 1990; 186: 1-5.

Klausner RD, Rouault TA and Harford JB. Regulating the fate of mRNA: the control of cellular iron metabolism. Cell 1993; 72: 19-28.

Haile DJ. Regulation of genes of iron metabolism by the iron-response proteins. Am J Med Sciences 1999; 318: 230-240.

Gatter KC, Brown G, Throwbridge IS, Woolston RE and Mason DY. Transferrin receptors in human tissues: their distribution and possible clinical relevance. J Clin Pathol 1983; 36: 539-545.

Faulk WP and Hung JS. Human placentae: view from an immunological bias. Am J Reprod Immunol 1990; 21: 108-113.

Broadwell RD, Baker-Caims BJ, Friden PM, Oliver C and Villegas JC. Transcytosis of protein through the mammalian cerebral epithelium and endothelium. III. Receptor mediated transcytosis through the blood-brain barrier of blood-borne transferrin and antibody against transferrin receptor. Exp Neurol 1996; 142: 47-65.

Ponka P, Beaumont C and Richardson DR. Function and regulation of transferrin and ferritin. Seminars in Hematol 1998; 35: 35-54.

Sylvester SR and Griswold MD. The testicular iron shuttle: A "nurse" function of the Sartoli cells. J Androl 1994; 15: 381-385.

Yeh CJG and Faulk WP. Killing of human tumor cells in culture with adriamycin conjugates of human transferrin. Clin Immunol Immunopath 1984; 32: 1-11.

Yeh CJG, Taylor CG and Faulk WP. Targeting of cytotoxic drugs by transferrin receptors: Selective killing of acute myelogenous leukemia cells. Protides Biol Fluids 1984; 32: 441-444.

Berczi A, Barabas K, Sizensky JA and Faulk WP. Adriamycin conjugates of human transferrin bind transferrin receptors and kill K562 and HL60 cells. Arch Biochem Biophys 1993; 300: 356-363.

Lai BT, Gao JP and Lanka KW. Mechanism of action and spectrum of cell lines sensitive to doxorubicin-transferrin conjugage. Cancer Chemother & Pharmacol 1998; 41: 155-160.

Kratz F, Beyer U, Roth T, Tarasova N, Collery P, Lechenault F, Cazabat A, Schumacher P, Unger C and Falken U. Transferrin conjugates of doxorubicin synthesis, characterization, cellular uptake, and in vitro efficacy. J Pharm Sciences 1998; 87: 338-346.

Tanaka T, Kaneo Y and Miyashita M. Synthesis of transferrin-mitomycin C conjugate as a receptor-mediated drug targeting system. Biol Pharm Bull 1996; 19: 774-777.

Sasaki K, Kohgo Y, Kato J, Kondo H and Niitsu Y. Intracellular metabolism and cytotoxicity of transferrin-neocarzinostatin conjugates of differing molar ratios. Jpn J Cancer Res. 1993; 84: 191-196.

Laske DW, Youle RJ and Oldfield EH. Tumor regression with regional distribution of the targeted toxin TF-CRM107 in patients with malignant brain tumors. Nature Med 1997; 3: 1362-1368.

Beyer U, Roth T, Schumacher P, Maier G, Unold A, Frahm AW, Fiebig HH, Unger C and Kratz F. Synthesis and in vitro efficacy of transferrin conjugates of the anticancer drug chlorambucil. J Med Chem 1998; 41: 2701-2708.

Bicamumpaka E and Page M. In vitro cytotoxicity of paclitaxel-transferrin conjugate on H69 cells. Oncol Reports 1998; 5: 1381-1383.

Lemieux P, Page M and Noel C. In vivo cytotoxicity and antineoplastic activity of a transferrin-daunorubicin conjugate. In Vivo 1992; 6: 621-627.

Guo M, Sun H, McArdle HJ, Gambling L and Sadler PJ. Ti(IV) uptake and release by human serum transferrin and recognition of Ti(IV)-transferrin by cancer cells: understanding the mechanism of action of the anticancer drug titanocene dichloride. Biochem 2000; 39: 10023-10033.

Shah D and Shen WC. Transcellular delivery of an insulin-transferrin conjugate in enterocyte-like Caco-2 cells. J Pharm Sciences 1996; 85: 1306-1311.

Drobyski WR, Ul-Haq R, Majewski D and Chitambar CR. Modulation of in vitro and in vivo T-cell responses by transferrin-gallium and gallium nitrate. Blood 1996; 88: 3056-3064.

Hoshino T, Misaki M, Yamamoto M, Shimizu H, Ogawa Y and Toguchi H. In vitro cytotoxicities and in vivo distribution of transferrin-platinum(II) complex. J Pharm Sciences 1995; 84: 216-221.

Ippoliti R, Ginobbi P, Lendaro E, D'Agostino I, Ombers D, Benedetti PA, Brunori M and Citro G. The effect of monensin and chloroquine on the endocytosis and toxicity of chioneric toxins. Cell Mol Life Sci 1998; 54: 866-875.

Kratz F, Hartmann F, Keppler B and Messor L. The binding properties of two antitumor ruthenium(III) complexes to apotransferrin. J Biol Chem 1994, 269: 2581-2588.

Park E, Starzyk RM, McGrath JP, Lee T, George J, Schutz AJ, Lynch P and Putney SD. Production and characterization of fusion proteins containing transferrin and nerve growth factor. J Drug Targeting 1998; 6: 53-64.

Ali SA, Joao HC, Hammerschmid F, Eder J and Steinkasserer A. Transferrin Trojan Horses as a rational approach for biological delivery of therapeutic peptide domains. J Biol Chem 1999; 274: 24066-24073.

Peters K and Richards FM. Chemical cross-linking: reagents and problems in studies of membrane structure. Annu Rev Biochem 1977; 46: 523-551.

Rhodes J. Evidence for an intercellular covalent reaction essential in antigen-specific T cell activation. J Immunol 1989; 143: 1482-1489.

Greenfield RS, Kaneko T, Daues A, Edson MA, Fitzgerald KA, Olech LJ, Grattan JA, Spitalny GL and Braslawsky GR. Evaluation in vitro of adriamycin immunoconjugates synthesized using an acid-sensitive hydrazone bond. Cancer Res 1990; 50: 6600-6607.

Braslawsky GR, Edson MA, Pearce W, Kaneko T and Greenfield RS. Antitumor activity of adriamycin (hydrazone-linked) immunoconjugates compared with free adriamycin and specificity of tumor cell killing. Cancer Res 1990; 50: 6608-6614.

O'Keefe DO and Draper RK. Characterization of transferrin-diphtheria toxin conjugate. J Biol Chem 1985; 260: 932-937.

Neidle S, Pearl LH and Skelly JV. DNA structure and perturbation by drug binding. Biochem J 1987; 243: 1-13.

Tritton TR. Cell surface actions of adriamycin. Pharmacol & Therapeutics 1991; 49: 293-309.

Maestre N, Tritton TR, Laurent G and Jaffrezou JP. Cell surface-directed interaction of anthracyclines leads to cytotoxicity and nuclear factor kappaB activation but not apoptosis signaling. Cancer Res 2001; 61: 2558-2561.

Fong WF, Lam W, Yang M and Wong JT-F. Partial synergism between dextran-conjugated doxorubicin and cancer drugs on the killing of multidrug resistant KV-V1 cells. Anticancer Res 1996; 16: 3773-3778.

Barabas K, Sizensky JA and Faulk WP. Transferrin conjugates of adriamycin are cytotoxic without intercalating nuclear DNA. J Biol Chem 1992; 267: 9437-9442.

Faulk WP, Barabas K, Sun IL and Crane FL. Transferrin-adriamycin conjugates which inhibit tumor cell proliferation without interaction with DNA inhibit plasma membrane oxidoreductase and proton release in K562 cells. Biochem Int 1991; 25: 815-822.

Berczi A, Ruthner M, Szuts V, Fritzer M, Schweinzer E and Goldenberg H. Influence of conjugation of doxorubicin to transferrin on the iron uptake by K562 cells via receptor-mediated endocytosis. Euro J Biochem 1993; 213: 427-436.

Barabas K, Sizensky J and Faulk WP. Evidence in support of the plasma membrane as the target for transferrin-adriamycin conjugates in K562 cells. Am J Reprod Immunol 1991; 25: 120-124.

Szuts V, Berczi A, Schweinzer E and Goldenberg H. Binding of doxorubicin-conjugated transferrin to U937 cells. J Receptor Res 1993; 13: 1041-1054.

Ruthner M, Berczi A and Goldenberg H. Interaction of a doxorubicin-transferrin conjugate with isolated transferrin receptors. Life Sci 1994; 54: 45-40.

Sainte-Marie J, Lafont V, Pecheur EI, Favero J, Philippot JR and Bienvenue A. Transferrin receptor functions as a signal-transduction molecule for its own recycling via increases in the internal Ca++ connection. Euro J Biochem 1997; 250: 689-697.

Klausner RD, vanReuswoude J, Ashwell G, Kempf C, Schechter AN, Dean A and Bridges K. Receptor-mediated endocytosis of transferrin in K562 cells. J Biol Chem 1983; 258: 4715-4724.

Richardson DR and Ponka P. The molecular mechanisms of a metabolism and transport of iron in normal and neoplastic cells. Biochem Biophy Acta 1997; 1331: 1-40.

Baker MA and Lawen A. Plasma membrane NADH-oxidase system: a critical review of the structural and functional data. Antioxidants & Redox Signaling 2000; 2: 197-212.

Sun IL, Navas P, Crane FL, Morre DJ and Low H. NADH-diferric transferrin reductase in liver plasma membranes. J Biol Chem 1987; 262: 15915-15921.

Sun IL, Navas P, Crane FL, Morre DJ and Low H. Diferric transferrin reductase in the plasma membrane is inhibited by adriamycin. Biochem Int 1987; 14: 119-127.

Faulk WP, Harats H, McIntyre JA, Berczi A, Sun IL and Crane FL. Recent advances in cancer research: Drug targeting without the use of monoclonal antibodies. Am J Reprod Immunol 1989; 21: 151-154.

Morre DJ, Kim C, Paulik M, Morre DM and Faulk WP. Is the drug-response NADH-oxidase of the cancer cell plasma membrane a molecular target for adriamycin? Bioenerg Biomembr 1997; 29: 269-280.

Sun IL, Sun EE, Crane FL, Morre DJ and Faulk WP. Inhibition of transplasma membrane electron transport by transferrin-adriamycin conjugates. Biochim Biophy Acta 1992; 1105: 84-88.

Crane FL, Low H, Sun IL, Morre DJ and Faulk WP. Interaction between oxidoreductase, transferrin receptor and channels in the plasma membrane. In: *Growth Factors from Genes to Clinical Applications* (eds, VR Sara, K Hall and H Low) Raven Press, New York, 1990; pp. 228-239.

Hileti D, Panayiotidis P and Hoffbrand V. Iron chelators induce apoptosis in proliferating cells. Brit J Haematol 1995; 89: 181-187.

Leardi A, Caraglia M, Selleri C, Pepe S, Pizzi C, Notaro R, Fabbrocini A, De Lorenzo S, Musico M, Abbruzzese A, Bianco A and Tagliaferri P. Desferioxamine increases iron depletion and apoptosis induced by ara-C of human myeloid leukemic cells. Brit J Haematol 1998; 102: 746-752.

Barabas K. Miller SJ and Faulk WP. Regulation of transferrin receptor mRNA stability in drug-sensitive and drug-resistant cancer cells. To be submitted for publication, 2003.

Hentze MW and Kuhn LC. Molecular control of vertebrate iron-metabolism: mRNA-based regulatory circuits operated by iron, nitric oxide and oxidative stress. Proc Natl Acad Sci USA 1996; 93: 8175-8182.

Pantapoulos K and Hentze MW. Rapid responses to oxidative stress mediated by iron regulatory protein. EMBO J 1995; 14: 2917-1924.

Wardrop SL, Watts RN and Richardson DR. Nitrogen monoxide activates iron regulatory protein 1 RNA-binding activity by two possible mechanisms: effect on the 4Fe-4S cluster and iron mobilization from cells. Biochemistry 2000; 39: 2748-2758.

Eisenstein RS. Iron regulatory proteins and the molecular control of mammalian iron metabolism. Annu Rev Nutr 2000; 20: 627-662.

Richardson DR, Naumannova, V, Nagy E and Ponka P. The effect of redox-related species of nitrogen monoxide on transferrin and iron uptake and cellular proliferation of erythroleukemia (K562) cells. Blood 1995; 86: 3211-3219.

Kim S and Ponka P. Effects of interferon-gamma and lipopolysaccharide on macrophage iron metabolism are mediated by nitric oxide-induced degradation of iron regulatory protein 2. J Biol Chem 2000; 275: 6220-6226.

Netsel FP, Green RN, Kickian K, Ponka P and Lapp WS. Activation of macrophage cytostatic effector mechanism during acute graft-versus-host disease: release of intracellular iron and nitric oxide-mediated cytostasis. Blood 2000; 96: 1836-1843.

Kim S and Ponka P. Control of transferrin receptor expression via nitric oxide-mediated modulation of iron-regulatory protein 2. J Biol Chem 1999; 274: 33035-33042.

Laske DW, Ilercil O, Akbasak A, Youle RJ and Oldfield EH. Efficacy of direct itratumoral therapy with targeted protein toxins for solid human gliomas in nude mice. J Neurosurg 1994; 80: 520-526.

Singh M, Atwal H and Micetich R. Transferrin directed delivery of adriamycin to human cells. Anticancer Res 1998; 18(3A): 1423-1427.

Sato Y, Yamauchi N, Takahashi M, Sasaki K, Fukaura J, Neda H, Fujii S, Hirayrna M, Itoh Y, Koshita Y, Kogawa K, Kato J, Sakamaski S and Niitsu Y. In vivo gene delivery to tumor cells by transferrin-streptavidin-DNA conjugate. FASEB Journal 2000; 14: 2108-2118.

Oldfield EH and Youle RJ. Immunotoxins for brain tumor therapy. Cur Top Microbiol Immunol 1998; 234: 97-114.

Kohgo Y, Kato J, Sasaki K and Kondo H. Targeting chemotherapy with transferrin-neocarzinostatin. Japanese J Cancer Chemotherapy 1988; 15: 1072-1076.

Faulk WP, Taylor CG, Yeh G and McIntyre JA. Preliminary clinical study of transferrin-adriamycin conjugate for drug delivery to acute leukemia patients. Mol Biother 1990; 2: 57-60.

Laske DW, Morrison PF, Lieberman DM, Carthesy ME, Reynolds JC, Stewart-Hermey PA, Koong SS, Cummins A, Paik CH and Oldfield EH. Chronic interstitial infusion of protein to primate brain: determination of drug distribution and clearance with single-photon emission computerized tomography imaging. J Neurosurg 1997; 87: 586-594.

Marbeuf-Gueye C, Ettori D, Priebe W, Kozlowski H and Garnier-Suillerot A. Correlation between the kinetics of anthracycline uptake and the resistance factor in cancer cells expressing the multidrug resistance protein or the P-glyooprotein. Biochem Biophy Acta 1999; 1450: 374-384.

Fritzer M, Barabas K, Szuts V, Berezi A, Szekeres T, Faulk WP and Goldenberg H. Cytotoxicity of a transferrin-adriamycin conjugate to anthracylcine resistant cells. Int J Cancer 1992; 52: 619-623.

Hatano T, Ohkawa K and Matsuda M. Cytotoxic effect of the protein-doxorubicin conjugates on the multidrug-resistant human myelogenous leukemia cell line, K562, in vitro. Tumor Biology 1993; 14: 288-294.

Lemieux P and Page M. Sensitivity of multidrug-resistant MCF-7 cells to a transferrin-doxorubicin conjugate. Anticancer Res 1994; 14(2A): 397-403.

Fritzer M, Szekeres T, Szuts V, Jraayam HN and Goldenberg H. Cytotoxic effects of a doxorubicin-transferrin conjugate in multidrug-resistant KB cells. Biochem Pharm 1996; 51: 489-493.

Wang F, Jiang X, Yang DC, Elliot RL and Head JF. Doxorubicin-gallium-transferrin conjugate overcomes multidrug resistance: evidence for drug accumulation in the nucleus of drug resistant MCF-7/ADR cells. Anticancer Res 2000; 20: 799-808.

Soma CE, Dubernet C and Barratt G. Ability of doxorubicin-loaded nanoparticles to overcome multidrug resistance of tumor cells after their capture by macrophages. Pharm Res 1999; 16: 1710-1716.

Mazel M, Clair P, Rousselle C, Vidal P, Scherrmann J-M, Mathieu D and Temsamani J. Doxorubicin-peptide conjugates overcome multidrug resistance. Anti-Cancer Drugs 2001; 12: 107-116.

Andreson BF, Baker HM, Norris GE, Rumball SV and Baker EN. Apolactoferrin structure demonstrates ligand-induced conformational change in transferrins. Nature 1990; 344: 784-787.

Baker EN. Structure and reactivity of transferrin. Adv Inorg Chem 1994; 41: 389-463.

Harris WR. Equilibrium constants for the complexation of metal ions by serum transferrin. Adv Exp Med & Biol 1989; 249: 67-93.

Li H, Sadler PJ and Sun H. Unexpectedly strong binding of a large metal ion ($Bi^{3+}$) to human serum transferrin. J Biol Chem 1996; 271: 9483-9489.

Battistuzzi G, Calzolai L, Messori L and Sola M. Metal-induced conformational heterogeneity of transferrins: a spectroscopic study of indium (III) and other metals (III)-substituted transferrins. Biochem Biophys Res Com 1995; 206: 161-170.

Kubal G, Mason AB, Patl SU, Sadler PJ and Woodworth RC. Oxolate- and $Ga^{3+}$-induced structural changes in human transferrin and its recombinant N-lobe. $^1$H NMR detection of preferential C-lobe $Ga^{3+}$ binding. Biochem 1993; 32: 3387-3395.

Grossman JG, Neu M. Evans RW, Lindley PF, Appeal H and Hasnain SS. Metal-induced conformational changes in transferrins. J Mol Biol 1993; 229: 585-590.

Sun H, Li H, Mason AB, Woodworth RC and Sadler PJ. N-lobe versus C-lobe complexation of bismuth by human transferrin. Biochem J 1999; 337: 105-111.

Dobson CB, Graham J and Itzhaki RF. Mechanism of uptake of gallium by human neuroblastoma cells and effects of gallium and aluminum on cell growth, lysosornal protease, and choline acetyl transferase activity. Exp Neurol 1998; 153: 342-350.

Abreo K, Jangula J, Jain SK, Sella M and Glass J. Aluminum uptake and toxicity in cultured mouse hepatocytes. J Am Soc Nephrol 1991; 1: 1299-1304.

Sun H, Li H, Mason AB, Woodworth RC and Sadler PJ. Competitive binding of bismuth to transferrin and albumin in aqueous solution and in blood plasma. J Biol Chem 2001; 276: 8829-8835.

Gallori E, Vettori C, Alessio E, Vilchez FG, Vilaplana R, Orioli P, Casini A and Messori L. DNA as a possible target for antitumor ruthenium complexes. Arch Biochem Biophy 2000; 376: 156-162.

Ward SG and Taylor RC. In, Metal-Based Anti-Tumor Drugs (Gielen MF, Ed) 1988, pp. 1-54, Fruend Publishing House Ltd., London.

Kubal G and Sadler PJ. Sequential binding of aluminum (3+) to the C- and N-lobe of human serum transferrin detected by $^1$H NMR spectroscopy. J Am Chem Soc 1992; 114: 1117-1118.

Kubal G, Mason AB, Sadler PJ, Tucker A and Woodworth RC. Uptake of $Al^{3+}$ into the N-lobe of human serum transferrin. Biochem J 1992; 285: 711-714.

Van Rensburg SJ, Carstens ME, Potocnik FCV and Taljaard JJF. The effect of iron and aluminum on transferrin and other serum proteins as revealed by isoelectric focusing gel electrophoresis. Annals NY Acad Sci 2000; 903: 150-155.

Kratz F, Hartmann M, Keppler B and Messori L. The binding properties of two antitumor ruthenium (III) complexes to apotransferrin. J Biol Chem 1994; 269: 2581-2588.

Guo M, Sun H, McArdle JH, Gambling L and Sadler PJ. $Ti^{IV}$ uptake and release by human serum transferrin and recognition of $Ti^{IV}$-transferrin by cancer cells: understanding the mechanism of action of the anticancer drug titanocene dichloride. Biochem 2000; 39: 10023-10033.

Roskams AJ and Cosmor JR. Aluminum access to the brain: a role for transferrin and its receptor. Proc Natl Acad Sci USA 1990; 87: 9024-9027.

Knorr GM and Chitamber CR. Gallium-pyridoxal isonicotinoyl hydrazone (Ga-PIH), a novel cytotoxic gallium complex. A comparative study with gallium nitrate. Anticancer Res 1998; 18 (3A): 1733-1737.

Kasai K, Hori MT and Goodman WG. Transferrin enhances the antiproliferative effect of aluminum on osteoblast-like cells. Am J Physiol 1991; 260 (4Pt1): E537-543.

McGregor SJ, Naves ML, Birly AK, Russell NH, Halls D, Junor BJ and Brock JH. Interaction of aluminum and gallium with human lymphocytes: the role of transferrin. Biochim Biophys Acta 1991; 1095: 196-200.

Abreo K and Glass J. Cellular, biochemical, and molecular mechanisms of aluminium toxicity. Nephrol Dial Transplant 1993; 8 Suppl 1: 5-11.

Kratz F, Mulinacci N, Messori L, Bertini I and Keppler BK. In, Metal Ions in Biology and Medicine, vol. 2, pp. 69-74, John Libbey Limited Eurotext, Paris, 1992.

WiSniewski MZ, Wietrzyk J and Opolski A. Novel Ru(III), Rh(III), Pd(II) and Pt(II) complexes with ligands incorporating azole and pyrimidine rings. I. Antiproliferative activity in vitro. Arch Immunolog Therap Exper 2000; 48: 51-55.

Frasca DR, Gehrig LE and Clarke MJ. Cellular effects of transferrin coordinated to. J Inorg Biochem 2001; 83: 139-149.

Whelan HR, Williams MB, Bijic DM, Flores RE, Schmidt MH, McAuliffe TL and Chitambar CR. Gallium nitrate delays the progression of microscopic disease in a human medulloblastoma murine model. Ped Neurol 1994; 11: 44-46.

Ganot PO. Metabolism and possible health effects of aluminum. Envir H1th Perspect 1986; 65: 363-441.

Keppler BK, Berger MR, and Heim ME. New tumor-inhibiting metal complexes. Cancer Treat Rev 1990; 17: 261-277.

Seeling MH, Berger MR and Keppler BK. Antineoplastic activity of three ruthenium derivatives against chemically induced colorectal carcinoma in rats. J Cancer Res Clin Oncol 1992; 188: 195-200.

Webster LK, Olver IN, Stokes KH, Sephton RG, Hillcoat BL and Bishop JF. A pharmacokinetic and phase II study of gallium nitrate in patients with non-small cell lung cancer. Cancer Chemother & Pharmacol 2000; 45: 55-58.

Brechbiel MW. Chelated metal ions for therapeutic and diagnostic applications. Exper Biol & Med 2001; 226: 627-628.

Veronese I, Guissani A, Cantono MC, de Bartolo D, Roth P and Werner E. Kinetics of systemic ruthenium in human blood using a stable tracer. J Radiol Protect 2001; 21: 31-38.

Crul M, van den Bongard HJ, Tibben MM, van Tellingen O, Sava G, Schellens JH and Beijnen JH. Validated method for the determination of the novel organo-ruthenium anticancer drug NAMI-A in human biological fluids by Zeeman atomic absorption spectrometry. Fersenius J Anal Chem 2001; 369: 442-445.

Howard JB and Ress DC. Perspectives on non-heme iron protein chemistry. Adv Protein Chem 1991; 42: 199-280.

Barabas K and Faulk WP. Transferrin receptors associate with drug resistance in cancer cells. Biochem Biophys Res Com 1993; 197: 702-708.

Luttropp CA, Jackson JA, Jones BJ, Sohn MH, Lynch RE and Morton KA. Uptake of Gallium-67 in transfected cells on tumors absent or enriched in the transferrin receptors. J Nucl Med 1998; 39: 1405-1411.

Pannccio M. Zalcberg JR, Thompson CH, Leyden JM, SullivanJR, Lichtenstein M and McKenzie IF. Heterogeneity of the human transferrin receptor and use of anti-transferrin receptor antibodies to detect tumors in vivo. Immunol & Cell Biol 1987; 65: 461-472.

Farley J, Loup D, Nelson M, Miller MJ, Taylor R and Gray K. Transferrin in normal and neoplastic endocervical tissues: distribution and receptor expression. Analyst & Quant Cytol & Histol 1998; 20: 238-249.

Sausville EA and Feigal E. Evolving approaches to cancer drug discovery and development at the National Cancer Institue, USA. Annals Oncol 1999; 10: 1287-1291.

Surolia N and Misquith S. Cell surface directed targeting of toxin to human malaria parasite. FEBs Lett 1996; 396:57-61.

Ohno H, Aguilar RC, Fournier M-C, Hennecke S, Cosson P and Biofacirio JS. Interaction of endocytic signals from the HIV-1 envelope glycoprotein complex with members of the adaptor medium chain family. Virology 1997; 238: 305-315.

Woodward JE, Bayer AL and Baliga P. Enhanced allograft survival via simultaneous blockade of transferrin receptor and interleukin-2-receptor. Transplantation 1999; 68: 136--1376.

Howard JB and Rees DC. Perspectives on non-heme iron protein chemistry. Adv Protein Chem 1991; 42: 199-280.

Barabas K and Faulk WP. Tranferrin receptors associate with drug resistance in cancer cells. Biochem Biophys Res Com 1993; 197: 702-708.

Pannccio M, Zalcberg JR, Thompson CH, Leyden JM, SullivanJr, Lichtenstein M and McKenzie IF. Heterogeneity of the human transferrin receptor and use of anti-transferrin receptor antibodies to detect tumors in vivo. Immunol & Cell Biol 1987; 65: 461-472.

Surolia N and Misquith S. Cell surface directed targeting of toxin to human malaria parasite. FEBS Lett 1996; 396:57-61.

Ohno H, Aguilar RC, Fournier M-C, Hennecke S, Cosson P and Boifacirio JS. Interaction of endocytic signals from the HIV-1 envelope glycoprotein complex with members of the adaptor medium chain family. Virology 1997; 238: 305-315.

Som P, Oster ZH, Matsui K, Guglielmi G, Persson BR, Pellettieri ML, Srivastrava SC, Richard P, Atkins HL and Brill AB: 97Ru-transferrin uptake in tumor and abscess. Eur J Nucl Med 1983; 8: 491-494.

Lambert JR. Pharmacology of bismuth-containing compounds. Rev Inf Dis 1991; 13(Suppl 8): S691-S695.

Pariente JL, Bordenave L, Bareille R, Ohayin-Courtes C, Baquey C and LeGuillou M. In vitro cytocompatibility of radio-opacifiers used in ureteral endoprosthesis. Biomaterials 1999; 20: 523-527.

Krari N, Mauras Y and Allain P. Enhancement of bismuth toxicity by L-cysteine. Res Com Mol Pathol & Pharmacol 1995; 89: 357-364.

Stoltenberg M, Schionning S and Danscher G. Retrogade axonal transport of bismuth: an autometrallographic study. Acta Neuropathol 2001; 101: 123-128.

* cited by examiner

TARGETED DELIVERY OF BIOAFFECTING COMPOUNDS FOR THE TREATMENT OF CANCER

CROSS REFERENCE TO RELATED APPLICATION

This application is a divisional of Ser. No. 10/477,998, filed Nov. 17, 2003, now U.S. Pat. No. 7,001,991, which is a 35 USC § 371 National Phase Entry Application from PCT/US02/11890, filed May 15, 2002, and designating the U.S, which claims priority benefit of U.S. Provisional Application Nos. 60/290,681 filed May 15, 2001, 60/291,016 filed May 16, 2001 and 60/291,015 filed May 16, 2001. The disclosure of the International Application and the three U.S. Provisional Applications are hereby incorporated by reference.

FIELD OF THE INVENTION

This invention relates generally to the field of bio-affecting materials useful in the treatment of diseased cells, such as cancer cells and, more specifically to a conjugate of a targeting agent and a bio-affecting material, where the bio-affecting material is a heat sensitizer, a photosensitizer or an apoptosis inducing compound.

BACKGROUND OF THE INVENTION

Two of the most devastating problems in cancer treatment are drug-toxicity, which debilitates patients, and drug-resistance, which is normally countered with even higher drug dosages and thus amplifies the problem of drug-toxicity, often resulting in death. One way to solve the problem of drug-toxicity is to target drugs for delivery only to cancer cells. Many researchers are working to develop antibodies to deliver drugs to targeted cells, and this approach holds promise, but antibodies are not without problems. For example, antibodies often bind to normal tissues, and they also can damage blood vessels (e.g., vascular leak syndrome) and cause dangerous allergic reactions (e.g. anaphylaxis).

Research is also progressing in connection with the use of conjugates of transferrin and doxorubicin, daunomycin, methotrexate, vincristin, 6-mercaptopurine, cytosine arabinoside, cyclophosphamide, and radioiodine as described in U.S. Pat. Nos. 5,108,987; 5,000,935; 4,895,714; and 4,886, 780. The inventions described in these patents does not use antibodies. Instead, it uses a protein found in normal human blood. This protein is transferrin, which delivers iron. Normal cells rarely require iron, but cancer cells require large amounts of iron to maintain their pathologically increased rates of metabolism. Because cancer cells require more iron, they have transferrin receptors substantially permanently on their surfaces, whereas normal cells do not. These inventions exploit these receptors by administering anticancer drugs conjugated with transferrin, which delivers the drugs substantially only to the surface of cancer cells.

Drug targeting spares normal cells, requires less drug, and significantly diminishes drug-toxicity. In contrast, when anticancer drugs are administered without being targeted, they kill normal cells as well as cancer cells. They are particularly toxic to cells of the immune system and to the system responsible for blood clotting. Thus, infections and bleeding are principal complications of chemotherapy in cancer patients. These complications require expensive services, hospitalizations, intensive care, and life-support systems, which are uncomfortable and expensive for the patient. These problems are largely preventable by using targeted delivery systems.

The problem of drug-toxicity consumes huge blocks of doctors' and nurses' time, and is responsible for much of the cost of cancer care. For example, it is commonly understood that about 70% of calls to oncologists relate to a problem of drug-toxicity. Today there is no satisfactory way to treat drug-toxicity, except to use less drug. In the absence of targeted delivery the use of less drug is counterintuitive in the case of drug resistant cancers. Targeted delivery allows the use of less drug, because more of the administered drug is delivered specifically to cancer cells rather than being nonspecifically distributed around the body. In this sense, targeted delivery is like shooting with a rifle, while conventional delivery is like shooting with a shotgun. A solution to the problem of drug-toxicity will dramatically transform chemotherapy in cancer patients. It is a purpose of this invention to reduce such adverse effects of chemotherapy.

The problem of drug-resistance is equally as serious as the problem of drug-toxicity. This problem is typified by a patient diagnosed with cancer who is treated and responds with a symptomless remission that lasts many months, and who later sees the cancer returns in a form that no longer responds to any known drug. This scenario of drug-resistance is all too common, Yet today there is no satisfactory solution, except the use of larger amounts of more powerful drugs, that in turn can cause serious drug-toxicity problems, often resulting in death. Thus, a solution to the problem of drug-resistance would significantly diminish the problem of drug-toxicity. A major effort was devoted to the use of P-glycoprotein inhibitors such as verapamil (Ford, Hematol/Oncol Clin N Am 1995; 9:337), cyclosporine (Bartlett et al., J Clin Oncol 1994; 12:835) and cyclosporine derivatives such as SDZ PSC 833 (Kusunoki et al., Jpn J Cancer Res 1999; 89:1220), and tamoxifen (Pommerenke et al., J Cancer Res Clin Oncol 1994; 120:422), but these approaches have not been clinically satisfactory because they introduced new problems in the pharmacokinetics of chemotherapy (Sikic et al., Cancer Chemother Pharmacol 1997; 40:S13). Other approaches are the design of MDR-reversing drugs (Naito & Tsuruo, Cancer Chemother Pharmacol 1997; 40:S20); the use of P-glycoprotein antisense oligonucleotides (Bertram et al., Anti-Cancer Drugs 1995; 6:124); the use of retrovirus-mediated transfer of anti-MDR ribozymes (Wang et al., Human Gene Therapy, 1999; 10:1185), and the design of chemotherapy drugs that are not removed from cancer cells by MDR or MRP pumps (Mankhetkorn et al., Mol Pharmacol 1996; 49:532), but none of this research has provided a solution to the clinical problem of drug resistance (Arceci, Br J Haematol 2000; 110:285). Another approach is to circumvent the MDR/MRP pumps by delivering anti-cancer drugs as conjugates of larger molecules such as albumin (Ohkawa et al., Cancer Res 1993; 53:4238), alpha-fetoprotein (Moskaleva et al., Cell Biol Int 1997; 21:793) and dextran (Fong et al., Anticancer Res 1996; 16:3773). Although these are variously effective at evading experimental drug resistance, they are unproven in patients. Protein-targeted drug delivery can overcome the problem of drug-resistance. Thus, another purpose of the present invention is to resolve the issue of painful and expensive deaths from drug-resistant cancers.

The effectiveness of proteins conjugated with bio-affecting molecules has been demonstrated and is described in the US patents mentioned above. It has been determined; however, that the efficiency of such conjugates in treating stressed cells, such as cancer cells, is reduced by the presence of agglutinated conjugates or by the presence of conjugates of a bio-affecting molecule with protein fragments or with two or three protein molecules and is greatly enhanced when the protein to bio-affecting molecule ratio is closer to 1:1 or 1:2, depending on the bio-affecting molecule. Obtaining conjugates of higher efficiency has, in the past, been a slow, tedious and expensive process that requires separating a fraction of conjugate having the desired average ratio of bio-affecting molecule to protein from a larger sample comprising such molecules conjugated with protein fragments, with a plurality of proteins and proteins conjugated with a plurality of bio-affecting molecules. Using homogeneous protein-drug conjugates in which the protein component carries a predetermined number of bio-affecting molecules can more effectively kill both drug-resistant and drug-sensitive cancer cells. In the past the expense and inefficiency inherent in producing useful conjugates in a useful volume has been a problem for the commercialization of such conjugates and for their widespread use in medicine. There is a need for a substantially homogeneous drug-protein conjugate and for a method of making such a conjugate that is more efficient, more precise and less costly. It is one purpose of this invention to provide such a homogeneous conjugate made by a more efficient method.

DESCRIPTION OF THE RELATED ART

The first report of transferrin receptors on human cancer cells was by Faulk and colleagues in 1980 (1). This was followed by many reports of transferrin receptors in different types of human cancers (2), as seen in the following Table.

| Tumor Studied | References | Tumor Studied | Reference |
|---|---|---|---|
| Breast | 1, 3 | Gastrointestinal | 10 |
| Leukemia | 4, 5 | Ovary | 11 |
| Lung | 6 | Non-Hodgkin's lymphoma | 12 |
| Brain | 7 | Lymphoma/melanoma | 13, 14 |
| Liver | 8 | Nasopharyngeal | 15 |
| Bladder | 9 | Cervix | 16 |

Transferrin Receptors on Normal and on Cancer Cells.

No single study has asked if all human cancers have up-regulated transferrin receptors, or if all normal cells have down-regulated transferrin receptors, but data from many quarters suggest that the answer to both questions is yes. For example, immature erythrocytes (i.e., normoblasts and reticulocytes) have transferrin receptors on their surfaces, but mature erythrocytes do not (17). Circulating monocytes also do not have up-regulated transferrin receptors (18), and macrophages, including Kupffer cells, acquire most of their iron by a transferrin-independent method of erythrophagocytosis (19). In fact, in vivo studies indicate that virtually no iron enters the reticuloendothelial system from plasma transferrin (for review, see reference 20). Macrophage transferrin receptors are down regulated by cytokines such as gamma interferon (21), presumably as a mechanism of iron-restriction to kill intracellular parasites (22).

In resting lymphocytes, not only are transferrin receptors down regulated, but the gene for transferrin receptor is not measurable (23). In contrast, stimulated lymphocytes up regulate transferrin receptors in late $G_1$ (24). Receptor expression occurs subsequent to expression of the c-myc proto-oncogene and following up-regulation of IL-2 receptor (25), and is accompanied by a measurable increase in iron-regulatory protein binding activity (26), which stabilizes transferrin receptor mRNA (27). This is true for both T and B lymphocytes (28), and is an IL-2-dependent response (29).

Cell stimulation resulting in the up regulation of receptors for transferrin is known to result from stress experienced, for example, by cells invaded by a viral or protozoan factor and by cancer cells.

Up-and-down regulation of transferrin receptors for normal and tumor cells has been shown by studies of antigen or lectin stimulation (i.e., receptor up-regulation), and by studies of differentiation models (30-33) using retinoic acid (i.e., receptor down-regulation). Base-line data from these experimental models suggest that these receptors are down-regulated from the plasma membranes of most normal, adult, resting human cells (34). Exceptions are the circulatory barrier systems, which include the materno-fetal barrier with its transferrin receptor-rich syncytiotrophoblast (35); the blood-brain barrier with its transferrin receptor-rich capillary endothelial cells (36); and, the blood-testis barrier with its transferrin receptor-rich Sertoli cells (37).

Transferrin-Drug Conjugates in Laboratory Animals

The efficacy of transferrin-drug conjugates has been investigated in several animal models. For example, conjugates of transferrin with diphtheria toxin decreased xenografted gliomas in nude mice by 95% on day 14, and the gliomas did not recur by day 30 (74). Also, glutaraldehyde-prepared transferrin-doxorubicin conjugates have been found to rescue nude mice from death by human mesothelioma cells, significantly prolonging life compared to animals treated only with doxorubicin (75). In addition, transferrin has been coupled to herpes simplex thymidine kinase by using biotin-streptavidin technology, and these conjugates significantly prolonged life in nude mice inoculated with metastasizing K562 tumor cells (76). Finally, the maximum tolerated dose of human transferrin-doxorubicin conjugates in nude mice has been found to be 20 mg/kg (iv) for conjugates and only 8 mg/kg (iv) for free drug (41).

Transferrin-Drug Conjugates in Human Patients

There are two clinical reports of transferrin-drug conjugates. The first, published in 1990, was a preliminary study of seven acute leukemia patients treated intravenously with 1 mg/day of glutaraldehyde-prepared transferrin-doxorubicin conjugates for 5 days. With these low doses, there were no toxic effects and the number of leukemic cells in peripheral blood of the 7 patients decreased by 86% within 10-days following therapy (77). In addition, there was no extension of disease as assessed by examination of bone marrow biopsies before and after treatment.

The second, published from the NIH in 1997, involved 15 patients with recurrent brain cancers treated with thioether-bonded transferrin conjugates of a genetic mutant of diphtheria toxin (44). The conjugates were delivered by high-flow interstitial microinfusion, which has been shown to produce effective perfusion of radiolabeled transferrin in primate brains with minimal inflammatory responses (78). Magnetic resonance imaging revealed at least a 50% reduction in tumor volume in 9 of the 15 patients, including 2 cases of complete remission (44).

There is an unpublished clinical study of 23 patients with advanced ovarian cancer who were randomized into test (12 patients) and placebo (11 patients) groups. The test group received transferrin-doxorubicin conjugates equivalent to 1 mg doxorubicin per day on days 15 through 19 of monthly treatment cycles. A significant difference was revealed by Cox regression estimates of survival rates for patients treated with transferrin-doxorubicin conjugates when the time between diagnosis and randomization was 18 months.

Another unpublished study is a 22-year old male with metastatic disease from a sarcoma of his right atrium who was treated by conventional protocols without response. His lungs were filled with metastatic lesions when his physician father obtained an IND from the FDA for the use of transferrin-doxorubicin conjugates, and treatment was begun in August, 2000. By November, the lungs were substantially cleared of metastatic lesions, and by January there was no radiological evidence of tumor. He presently (May 2002) is active, receiving only transferrin-doxorubicin.

The targeted delivery of drugs has the advantage of increasing efficacy while using less drug, thereby decreasing toxicity and causing less damage to normal cells, all of which effectively decrease costs and increase the quality of patient care. Targeted delivery also avoids drug-resistance, which is activated by the non-specific entrance of drugs into cells (79). Because transferrin-drug conjugates can enter cells specifically by employing a receptor-specific pathway (80,81), they are trafficked around drug-resistance mechanisms, such as efflux pumps in resistant cells.

It was reported in 1992 that transferrin-doxorubicin conjugates effectively kill multi-drug resistant cells (82). This finding was confirmed in 1993 (83), and was extended to several types of drug-resistant cells in 1994 (84), 1996 (85) and 2000 (86). Interestingly, doxorubicin immobilized on solid carriers also has been shown to be effective against doxorubicin-resistant cells (60,87). In fact, a concept is emerging that vectorization of doxorubicin with one of several peptide vectors is effective in overcoming multi-drug resistance (88).

Preparation of Transferrin-Drug Conjugates.

A method for the preparation of transferrin-doxorubicin conjugates was published first in 1984 (38), following which there have been many reports of methods for the preparation of transferrin-drug conjugates, some of which are listed in the following Table.

| Transferrin Label | Method Used | References | Transferrin Label | Method Used | References |
| --- | --- | --- | --- | --- | --- |
| Doxorubicin | Glutaraldehyde | 38,39,40 | Titanium | Carbonate | 48 |
| Doxorubicin | Maleimide | 41 | Insulin | Disulfide | 49 |
| Mitomycin C | Glutaryl Spacer | 42 | Gallium | Carbonate | 50 |
| Neocarzinostatin | Succinimide | 43 | Platinum | Methionine | 51 |
| Diphtheria Toxin | Thioester | 44 | Saporin/ricin | Succinimide | 52 |
| Chlorambucil | Maleimide | 45 | Ruthenium | Bicarbonate | 53 |
| Paclitaxol | Glutaraldehyde | 46 | Growth Factor | Fusion Protein | 54 |
| Daunorubicin | Glutaraldehyde | 47 | HIV Protease | Recombinant | 55 |

Transferrin conjugates of doxorubicin have been prepared by using glutaraldehyde-mediated Schiff base formation (56, 57), which forms an acid-resistant bond between epsilon-amino lysine groups of transferrin and the 3'amino position of doxorubicin. Such conjugates of doxorubicin can kill cancer cells through a plasma membrane-mediated mechanisms (for review, see reference 58). Although DNA intercalation is an established mechanism of cell death by doxorubicin, immobilized doxorubicin conjugated with proteins capable of binding with receptors on the cell surface activate plasma membrane-mediated mechanisms to kill cells (59,60). It thus appears that conjugates of doxorubicin with transferrin kill cells by activating plasma membrane-mediated mechanisms that involve both doxorubicin and transferrin receptors.

SUMMARY OF THE INVENTION

It is apparent that targeting agent-drug conjugates have a generic possibility of changing how drugs are delivered, as well as a specific possibility of changing how drugs are delivered to cancer patients. In the present invention, non-antibody proteins such as transferrin, ceruloplasmin, vitamin binding proteins such as transcobalamin, hormones, somatostatin, cytokines, low density lipoproteins, growth factors, growth factor-like molecules, are used as targeting agents in combination with anti-cancer compounds. Because transferrin and transcobalamin are excellent carriers for delivering compounds into drug-sensitive and drug resistant cancer cells, the targeted delivery system in the present invention preferably consists of transferrin or transcobalamin coupled to anticancer compounds selected from the group consisting of heat sensitizers, photosensitizers and apoptosis inducing compounds.

DETAILED DESCRIPTION OF THE INVENTION

The present invention relates to conjugates with a targeting agent and an antitumor agent. The targeting agents according to the present invention include but are not limited to transferrin, ceruloplasmin, somatostatin, vitamins, vitamin binding proteins such as transcobalamin, hormones, cytokines, low density lipoproteins, growth factor-like molecules, folic acid-like molecules and growth factors. The anti-tumor agents include but are not limited to heat sensitizers such as hematophorphyrine and low-dose verapamil, apoptosis inducing compounds such as deferoxamine, and photosensitizers such as porfimer sodium, metatetrahydroxyphenylchlorin, and hematophorphyrin derivatives. Preferably the targeting agent is transferrin or transcobalamin. Preferably the anti-tumor agent and the targeting agent are conjugated by means of a linker. Suitable linkers include but are not limited to glutaraldehyde (Bérczi et al., Arch Biochem Biophys 1993; 300: 356), disulfide coupling (Sash et al., Jap J Cancer Res 1993; 84: 191) and benzoyl hydrazone (Kratz et al., J Pharm Sci 1998; 87: 338).

Transferrin-Heat Sensitizer Conjugates.

Hyperthermia is widely used in cancer treatment either alone or in combination with chemotherapy and radiotherapy (Kong et al., Int J Hyperthermia 1999; 15: 345; Raaphorst et al., Oncology Reports 1998; 5: 971; Mager et al., Anticancer Res 1999; 19: 3403). In combination treatments, hyperthermia (41-45° C.) has been shown to be an effective radiation sensitizer (Sukurai et al., Int J Rad Biol 1999; 75: 739; Harima et al., Cancer 2000; 88: 132). Heat enhances the cytotoxic effect of certain anticancer agents such as bleomycin (Khadir et al., Arch Biochem Biophys 1999; 370: 163), carboplatin (Steller et al., Cancer Chemother Pharmacol 1999; 43: 106), doxorubicin (Kawai et al., Cancer 1997; 79: 214) and cisplatin (Raaphoist et al., Oncol Reports 1998; 5: 971; Benoit et al., Chirurgie 1999; 124:375). Hyperthermia is used in some therapy-resistant malignancies (Wessalowski et al., Int J Hyperthermia 1999; 15: 455) and high temperature hyperthermia (greater than 50° C.) has been used for selective tissue destruction as an alternative to conventional invasive surgery (Diederich et al., Ultrasound In Med Biol 1999; 25: 871).

The effectiveness of hyperthermia is strongly dependent on the ability to localize and maintain therapeutic temperature elevations (Diederich et al., Ultrasound In Med Biol. 1999; 25: 871). To achieve better results, several techniques have been used to produce controlled temperature increases in tissue. Some of these techniques involve the use of YAG Lasers (Graeber et al., Laryngoscopy 1999;109: 447), radiofrequences (Wust et al., Int J Hyperthermia 1998;14: 459), ultrasound (Diederich et al., Ultrasound In Med Biol 1999; 25: 87 I), and microwaves (Finger, Ophthalmol 1997;104: 1794). Hyperthermia is more effective at high temperatures, but its use is limited by the need to protect healthy tissues from heat damage.

Heat induces toxic characteristics in several compounds that are not toxic at normal body temperature. An example of this is hematophorphyrine. At 41.5° C. this molecule is a potent heat (or hyperthermia) sensitizer, and its ability to sensitize increases in a dose-dependent manner (Saito et al., Int J Hyperthermia 1998;14: 503). Another example of a heat (or hyperthermia) sensitizers is the use of low-dose verapamil at 42° C. (Shchepotin et al., Int J Hyperthermia 1997;13: 547). Heat sensitizers do not elevate local temperatures. They function by producing increased local toxicity in the presence of heat. If non-toxic compounds that produce toxicity at higher than body temperature, or toxic compounds that increase their toxicities at elevated temperature, could be delivered only to cancer cells, then hyperthermia could be used more efficiently to treat cancer. Such a targeted delivery system would not damage healthy tissues, which would receive only the effects of elevated temperatures.

This invention introduces a way of selectively delivering compounds that are highly toxic for cancer cells at increased temperatures. This targeted delivery system involves the use of transferrin as the carrier of the heat (or hyperthermia) sensitizer.

The use of targeted delivery of heat sensitizers would make the outcome of hyperthermia more effective by itself or in combination with other treatments, since heat sensitive toxicity can be concentrated in cancer cells. In this way, damage of healthy tissues is minimal, as most sensitizers can work at relatively low temperatures (e.g., 41-42° C.).

Since transferrin is an excellent carrier for delivering compounds to drug-sensitive and drug resistant cancer cells, the targeted delivery system in this invention consists of transferrin coupled to heat sensitizers. Transferrin for use in human patients is commercially available (for example, from the Finnish Red Cross). Several coupling processes such as glutaraldehyde coupling (Bérczi et al., Arch Biochem Biophys 1993; 300: 356), disulfide coupling (Sash et al., Jap J Cancer Res 1993; 84: 191) and benzoyl hydrazone coupling (Kratz et al., J Pharm Sci 1998; 87: 338) have been used to couple transferrin with other compounds. The broad variety of coupling procedures allow the conjugation of a wide range of sensitizers to transferrin, resulting in either permanent or dissociable bonding of sensitizers with the transferrin molecule. Following the conjugation of transferrin to the selected heat sensitizer, the conjugates should be separated from the uncoupled components, for example by using chromatographic and/or dialysis techniques. Examples of suitable heat sensitizers include but are not limited to doxorubicin, cisplatin and hematophosphrine.

Transferrin-Photosensitizer Conjugates

Photochemotherapy of cancer often is called photodynamic therapy (PDT). This form of therapy arose in the late 1970s and appeared as an alternative form of treatment for localized inoperable lesions (Dougherty et al., Cancer Res 1978; 38:2628). It involves the administration a tumor-localizing agent (Hayata et al., Chest 1982; 81:269), which may require metabolic changes (e.g., a prodrug), followed by activation of the agent by light of a specific wavelength (Sharman et al., Meth in Enzymol 2000; 319:376). This results in production of a sequence of photochemical and photobiological reactions, such as the production of singlet oxygen (Yuan et al., Radiation Res 1997; 148:386) that initiate tumor necrosis (Ochsner, J Photochem Photobiol 1997; 39: 1) via thrombosis (Henderson & Dougherty, J Photochem Photobiol 1992; 55:145) and apoptosis (Luo & Kessel, Biochem Biophys Res Corn 1996; 221:72).

Progress in PDT during the 1990s has included development of more efficient photosensitizers that absorb at longer wavelengths and require less energy for activation, thus allowing deeper penetration. New fiber optics also have been developed that allow illumination of difficult geometric configurations, and smaller, less expensive and more mobile lasers have become more readily available. This research and development has allowed PDT to evolve into a more widely used therapeutic modality, both for the primary treatment of cancer and for an adjunct to surgical debulking of larger tumors Treatment with PDT has been used in a wide variety of cancers, including basal cell carcinomas (Stefanidon et al., Euro J Dermatol 2000; 10:351), lymphomas (Orenstein et al., Dermatol Surg 2000; 26:765), stomach cancer (Gassner et al., Gastrointest Endoscop Clin N Am 2000; 10:461) and leukemia (Danilatou et al., Leukemia Res 2000; 24:427). Indeed, a recent review lists more than 60 types of cancer that have been treated with the FDA-approved photosensitizer Photofrin (porfimer sodium). In addition to its use in cancer treatment, PDT also has been used in Dermatology (Hongcharu et al., J Invest Dermatol 2000; 115:183), Ophthalmology (Tannous et al., Invest Ophthal Visual Sci 2000; 41:749), and recently PDT has been used in angioplasty procedures (Rockson et al., Circulation 2000; 102:591).

The first photosensitizer to receive FDA approval was Photofrin, produced by QLT Photo Therapeutics in Canada. Another widely studied photosensitizer is aminolevulinic acid. Other molecules in clinical trials are SnET2, which is a chlorin photosensitizer produced as Purlytin by Pharmacia/Upjohn. Another molecule is mTHPC produced by Scotia Pharmaceuticals as Foscan, which is a metatetrahydroxyphenylchlorin. Macular degeneration has been inhibited by using the photosensitizer Verteporfin, which is a haematophorphyrin derivative. These and several other molecules used as photosensitizers have been reviewed by Stewart and colleagues (Radiother Oncol 1998; 48:233) and by Dougherty and colleagues (J Natl Cancer Inst 1998; 90:889).

Since the presence of transferrin receptors is restricted principally to the surface of tumor cells, as originally described by Faulk and colleagues in the Lancet (1980; 2:390), the use of transferrin as the carrier of photosensitizers virtually assures that the drug will be targeted only to cancer cells, thus allowing the effects of PDT to be localized to the tumor and only to the tumor. In addition to minimizing collateral damage of normal cells, targeting of the photosensitizer drugs as conjugates of transferrin allows the use of lower doses of drugs, which will diminish the side effects of some drugs. For example, solar photosensitivity is a dose-related problem encountered in some patients treated with Photoprin.

The present invention of targeting the delivery of photosensitizer drugs as conjugates of transferrin to transferrin receptors on the surface of cancer cells has several advantages that derive from the biology of the carrier. The foremost of these is the property of transferrin drug conjugates to cross the blood-brain-barrier (Broadwell et al., Exp Neurol 1996; 142: 47). This property is endowed in the molecule by the normal presence of transferrin receptors on the luminal surface of endothelial cells that provide the microcirculation of the blood-brain-barrier (Moos & Morgan, Cell Mol Neurobiol 2000; 20:77). This has been utilized to deliver molecules from the blood circulation into the brain as conjugates of transferrin (Park et al., J Drug Target 1998; 6:53), which allows for the targeted use of PDT in patients with brain cancer. Another biological property of transferrin that positions it as an ideal carrier for photosensitizer drugs is that it is endocytosed into cells after being bound by transferrin receptors (Berczi et al., Eur J Biochem 1993; 213:427). This property can localize photosensitizers to the inside of cancer cells, which concentrates the drug and augments killing. In this regard, it is relevant that doxorubicin conjugates of transferrin have been used to kill doxorubicin-resistant cancer cells that were not killed by 10-fold higher concentrations of free doxorubicin (Fritzer et al., Int J Cancer 1992; 52:619).

In the following discussion transferrin is illustrative of the targeting protein. Transferrin can be isolated from normal blood plasma, purchased from any of several companies, including both the American and Finnish Red Cross, or be prepared from recombinant technology (Ali et al., J Biol Chem 1999; 274:24066). To form a drug:transferrin conjugate, the transferrin molecule must be modified in such a way as to prepare it to be coupled with a photosensitizer drug. For example, transferrin must be thiolated in order to form maleimide derivatives of drugs (Kratz et al., J Pharm Sci 1998; 87:338). The exact method of conjugation will depend upon the chemistry of the photosensitizer to be coupled with transferrin. For example, Protofrin is a polyporphrin containing ester and ether linkages, suggesting one type of carrier (Dubowchik & Walker, Pharmacol & Therap 1999; 83:67), other drugs contain NH2-groups that can be coupled to transferrin by using bifunctional reagents such as glutaraldehyde, and others require disulfide coupling (Sasaki et al., Jap J Cancer Res 1993; 84:191). The wide variety of coupling procedures allows the conjugation of a broad range of photosensitizer drugs with transferrin, resulting in either permanent or dissociable bonding of drugs with the transferrin molecule (Barabas et al., J Biol Chem 1992; 267:9437). Whatever procedure is used, after the coupling reaction the drug-protein conjugates must be separated from uncoupled drug and/or free protein, preferably by using chromatography or dialysis techniques.

Transferrin-Apoptosis Inducing Compound Conjugates

A mechanism for iron-restricted cytotoxicity in cancer is the potentiation of programmed cell death. Deferoxamine has been found to increase arabinoside-mediated apoptosis of human myeloid leukemia cells (Leardi et al., Br J Haematol 1998; 102:746). There is considerable evidence that a major pathway for apoptosis involves calcium-mediated downstream signaling subsequent to ligand-binding of programmed cell death surface receptor CD95 (Kass & Orrenius, Environ Health Perspec 1999; 107(Suppl 1):25). Similarly, the transferrin receptor functions as a signal-transduction molecule for its own recycling by increasing intracellular free calcium concentrations (Sainte-Marie et al., Europ J Biochem 1997; 250:689). Taken together, these apparently unrelated observations indicate a hitherto undescribed relationship between calcium, iron and transferrin receptors in drug resistant cancer cells.

In order to test the relationship between calcium and transferrin receptors, the effect of calcium channel inhibitors on the regulation of transferrin receptors was studied in drug-sensitive and drug-resistant cancer cells. The results of these experiments show that both organic (e.g. verapamil) and inorganic ($CdCl_2$) calcium channel blockers cause differential effects on the regulation of transferrin receptors. For example, both types of channel blockers initiated down-regulation of receptors, but more down-regulation was observed on drug-resistant cells than on drug-sensitive cells. Since the half-life of down-regulation was about eight hours, the decrease of surface receptors did not result from inhibition of exocytosis. The addition of free iron or transferrin-bound iron also had a differential effect on the down-regulation of transferrin receptors. The effect was similar but even more pronounced, namely iron down-regulated receptors much more on drug-resistant cells than on drug-sensitive cells, and produced about the same half-life as calcium channel blockers. The addition of both iron and calcium channel blockers had no effect on cell viability.

In light of the above findings, another series of experiments were done to determine whether the restriction of iron by deferoxamine had differential effects on drug-sensitive and drug-resistant cancer cells. The results of these experiments revealed that low concentrations of deferoxamine up-regulated transferrin receptors on both drug-sensitive and drug-resistant cells, but increasing concentrations of deferoxamine decreased transferrin receptor expression by drug-resistant cells, and viability experiments showed that the higher concentrations killed drug-resistant but not drug-sensitive cells. For example, after 48 hours in a given concentration of deferoxamine, drug-sensitive cells showed 93% viability, but only 16% of drug-resistant cells were alive. In summary, these three different types of experiments revealed a marked instability of transferrin receptor regulation in drug-resistant cells, and showed that iron depletion rapidly caused death of the drug-resistant cells.

The present invention is a way to target and kill drug-resistant cells in cancer patients. In a preferred embodiment, a conjugate of a drug carrier that targets an iron chelator to drug-resistant cancer cells is prepared. Transferrin is a normal blood protein that is well suited to deliver an iron chelator, because tumor cells have transferrin receptors on their surface and normal, adult, resting cells do not (Berczi et al., Arch Biochem Biophys 1993; 380:356). There are many iron chelators that can be conjugated with transferrin and delivered to drug-resistant cancer cells (Tsafack et al., Mol Pharmacol 1995; 47:403), but the chemistry of deferoxamine renders it well suited for conjugation to transferrin (Tsafack et al., J Lab Clin Med 1976; 127:574). Several conjugation or coupling procedures are possible to couple the targeting agent with other compounds, including but not limited to glutaraldehyde (Yeh & Faulk, Clin Immunol Immunopathol 1984; 32:1), disulfide coupling (Sasaki et al., Jap J Can Res 1993; 84:191) or benzoyl hydrazone coupling (Kratz et al., J Pharm Sci 1998; 87:338). The wide variety of coupling procedures allows the conjugation of a broad range of iron-chelating drugs to targeting proteins, resulting in either permanent or dissociable bonding of cytotoxic drugs with the protein molecule (Barabas et al., J Biol Chem 1992; 267:9437). Following the coupling reaction, drug-protein conjugates can be separated from uncoupled drug and free protein, preferably by using chromatographic or dialysis procedures.

Technical details of the conjugation procedure can vary, but the conjugates must be active in binding and killing experiments with cancer cells, and should not bind or kill significant numbers of normal cells. In light of these requirements, the preferred method for preparing the conjugates according to the present invention is the following process:

The synthesis of large amounts of homogeneous transferrin-doxorubicin conjugates with predetermined molecular ratios was done stoichiometrically by employing the only amino group of doxorubicin (DOX), which is at the 3' amino position, to react with one of the two reactive groups on glutaraldehyde (GLU) by drop-wise addition of a saline solution of DOX into a saline solution of GLU containing a solvent such as DMSO or another suitable cryopreservative, to a final concentration of a 1:1 molar ratio of DOX-to-GLU. The resulting solution of DOX-GLU was stirred three hours at room temperature in the dark.

The molarities of DOX and GLU were the same in the above reaction in order to produce a final solution of DOX-GLU that contains neither free DOX nor free GLU. However, there is the possibility of free GLU in solution if one GLU reacts with two DOX to produce DOX-GLU-DOX, but this possibility is minimized by the mass action kinetics generated by drop-wise addition of monovalent DOX into the solution of bivalent GLU. The volumes of these reactants are not restricted, so large amounts of homogeneous DOX-GLU can be prepared.

The DOX-GLU was conjugated with a targeting protein by drop-wise addition to a saline solution of transferrin (TRF). The TRF can be either iron-free (apo-transferrin) or iron-saturated (holo-transferrin). The desired molar ratio of DOX to TRF was obtained by appropriately adjusting the volume of TRF. The resulting solution of TRF-GLU-DOX was stirred for 20 hours at room temperature in the dark. Unlike the reaction of DOX with GLU, the reaction of DOX-GLU with TRF is not restricted to one binding site, for the GLU component of DOX-GLU can react with any one of several epsilon-amino lysine groups in the TRF molecule.

The number of DOX molecules bound to TRF was determined by calculation. For example, if the starting ratio of DOX-GLU to TRF was 7.2:1.0, the final solution of TRF-GLU-DOX would have contained 2.5 molecules of DOX per molecule of TRF. However, if the starting ratio of DOX-GLU to TRF was 4.0:1.0, the final solution of TRF-GLU-DOX would have contained 1.4 molecules of DOX per molecule of TRF. Similarly, if the starting ratio of DOX-GLU to TRF was 2.5:1.0, the final solution of TRF-GLU-DOX would have contained 0.9 molecules of DOX per molecule of TRF. In this way, large amounts of TRF-GLU-DOX with predetermined ratios of DOX-to-TRF can be provided according to the need.

Further steps in the conjugation reaction were the addition of ethanolamine or another substance suitable for scavenging any excess linker, followed by centrifugation and dialysis. Although reactions with DOX and TRF theoretically consume all of the GLU, ethanolamine was added to the final reaction mixture to bind any available GLU. This reaction was allowed to continue for 30 minutes in the dark. The final solution was centrifuged at 2000 rpm for 10 minutes, dialyzed twice for 6 hours in a 100-fold excess of saline and three times in the same excess of Hepes buffered saline, and the resulting TRF-GLU-DOX conjugates were ready for use. Biochemical Characterization of the Conjugates:

By using HPLC and polyacrylamide gel electrophoresis as described in (39), the homogeneity of TRF-GLU-DOX conjugates can be determined. Also, by using spectrophotometry as described in (89), the molecular ratio of DOX-to-TRF can be determined. These techniques repeatedly have revealed a consistent homogeneity of the TRF-GLU-DOX conjugates. In addition, chromatography is not required in the preparation of these conjugates, because there are no aggregates or fragments. This allows for the preparation of large volumes of homogeneous transferrin-drug conjugates, which increases yields and decreases costs.

The expenses caused by losses of TRF and DOX in other types of transferrin-drug conjugates have been an impediment to their use. For example, yields of DOX and TRF are decreased by using procedures such as thiolation (44) that alter the drug and/or protein. Yields also are decreased by using solvent systems (86) and by chromatography used to prepare acid-stable and acid-labile linkages (41). The GLU bond between DOX and TRF is acid-stable (89), and yields of DOX and TRF in TRF-DOX conjugates prepared according to this invention are high. Indeed, compared to other procedures (38, 39, 40), the yield for TRF is nearly doubled (90% vs 50%), and the yield for DOX is increased 5-fold.

None of the previously known approaches to the preparation of transferrin-doxorubicin conjugates are capable of producing large amounts of homogeneous conjugates with predetermined ratios of the number of drug molecules per molecule of transferrin. In addition, the other approaches employ chromatography to eliminate aggregates and to harvest fractions that are enriched in homogeneous conjugates. These procedures decrease yields, increase costs, and lack the ability to predetermine molecular ratios.

Another procedure would be to mix one milliliter of transferrin (0.5 mM) with one milliliter of deferoxamine (8.5 mM) in 150 mM sodium chloride for 4 minutes, and then add one milliliter of 21.5 mM glutaraldehyde in 150 mM sodium chloride and mix 4 minutes. The preceding reaction is a coupling procedure, which is stopped by the addition of 0.8 milliliters of 37.2 mM ethanolamine in 150 mM sodium chloride and 10 mM Hepes buffer (pH8) and vortexed for 4 minutes. The mixture (3.8 milliliters) then is transferred to dialysis tubing (molecular weight cutoff of 12,000-14,000), and dialyzed against 0.5 liters of Hepes-buffered saline in the dark at 5° C. for 3 hours. The dialysis should be repeated at least once with fresh Hepes-buffered saline. The mixture then is centrifuged at 1600 g for 10 minutes at 4° C. and the supernatant is chromatographed at a flow rate of 22 milliliters per hour on a 2.6×34 cm column of Sepharose CL-4B, previously equilibrated in Hepes-buffered saline and calibrated at 5° C. with blue dextran, transferrin and cytochrome C. Elution from the column is monitored at 280 nm, and 3.8 milliliter fractions are collected. The concentration of transferrin and deferoxamine in each fraction is calculated by successive approximation from standard curves from transferrin and deferoxamine, determined by using 280 nm for transferrin and 356 nm for deferoxamine. With minor modifications, this coupling procedure can be used to prepare targeting protein conjugates of other iron chelating drugs, such as protein conjugates of hydrophobic reversed siderophores.

Characterizing the Conjugates

After the pure drug-protein conjugates are isolated, they are characterized by polyacrylamide gel electrophoresis to determine their molecular weight, and the number of drug molecules per protein molecule is determined. The exact number of drug molecules per transferrin molecule can be determined, using any suitable technique including but not limited to spectrophotometric techniques. A functional drug:protein ratio is between about 0.1:1.0 to 3.0:1.0 (Berczi et al., Arch Biochem Biophys 1993; 300:356). The conjugates are checked to determine if they bind to receptors on the surface of tumor cells, and to determine if the conjugates kill cancer cells but not normal cells. Only conjugates that bind to cancer cells and not to normal cells are selected for toxicity tests using drug-sensitive and drug-resistant cancer cells. The binding studies can be done by using flow cytometry or any other suitable method, and the killing studies can be done by using microculture techniques to determine the concentration of free drug required to kill 50% of a culture of cancer cells compared to the concentration of drug in the drug-protein conjugates required to kill the same number of cancer cells. When testing the heat sensitizer conjugates, the toxicity test is done by using the MIT tetrazolium colorimetric assay (Visitica et al., Cancer Res 1994; 51: 2515). These toxicity tests determine the most potent transferrin sensitizer ratio and the optimum concentration of conjugate for maximum heat sensitization of drug sensitive and drug resistant cells. Approximately 10-fold more free drug compared to drug in the drug-protein conjugate is required to kill the same number of cells.

While the above description refers to transferrin as being the delivery protein, it is known that other proteins exist in the body which are capable of binding to receptor sites on cells. If such a receptor site is activated in cancer cells and is inactive in normal cells, then any protein or other molecule (i.e., ligand) that binds to such a receptor site can be used to deliver the drugs used in the present invention. An example of such a binding protein is transcobalamin, which delivers vitamin B 12 to transcobalamin receptors on cells, including cancer cells (Seetheram, Ann Rev Nutr 1999; 19:173). Low density lipoprotein is another ligand that has been conjugated to the photosensitizer chlorin and targeted to low density lipoprotein receptors on retinoblastoma cells (Schmidt-Erfurth et al., Brit J Surg 1997; 75:54).

After the drug-protein conjugate has been prepared, purified, characterized and validated for cellular binding and killing properties, and, when the binding and killing experiments show that the conjugate binds to and kills cancer but not normal cells, the conjugate is then aliquoted and sterilized. The sterilization process can be done by any suitable method including but not limited to exposure to irradiation, such as by using a cesium irradiator, or by using Millipore filtration techniques.

According to a further aspect of the present invention, there is provided a reagent kit for the treatment of tumors, comprising iron-bearing transferrin and a conjugate of transferrin with either a photosensitizer, a heat sensitizer agent or an apoptosis inducing compound. The patient's normal cells which have transferrin receptors may be protected against the effects of the conjugate by saturating these receptors with the iron-bearing transferrin before administration of the photosensitizer, heat sensitizer or apoptosis inducing conjugates.

The present invention also provides a process for determining the susceptibility of tumor cells to anti-tumor agents, comprising administering separately to portions of said tumor cells conjugates of transferrin with a number of different photosensitizer, heat sensitizer and/or apoptosis inducing agents. A reagent kit comprising a number of such different conjugates may be provided for this purpose. It has been found that tumor cells take up the conjugates of the present invention extremely rapidly. This means that within a matter of hours of removal from the patient, tumor cells may be tested against a range of conjugates of transferrin with different anti-tumor agents. Such a process would enable the chemotherapy which is most effective for a given patient to be determined as soon as possible after isolation of the tumor cells.

The conjugates according to the present invention are administered to an animal in an effective amount. In treating cancer, an effective amount includes an amount effective to: reduce the size of a tumor; slow the growth of a tumor; prevent or inhibit metastases; or increase the life expectancy of the affected animal. The present invention provides for a method of treating cancers wherein the cancer can be but is not limited to a leukemia, breast cancer, ovarian cancer, pancreatic cancer, lung cancer, bladder cancer, gastrointestinal cancer, nasopharyngeal cancer, cervical cancer, sarcoma, myeloma, lymphoma/melanoma, glioma, or astrocytoma. The dosage for the conjugates can be determined taking into account the age, weight and condition of the patient and the pharmacokinetics of the anti-tumor agent. The amount of the conjugate required for effective treatment will be less than the amount required using the anti-tumor agent alone.

The pharmaceutical compositions of the invention can be administered by a number of routes, including but not limited to orally, topically, rectally, vaginally, by pulmonary route, for instance, by use of an aerosol, or parenterally, including but not limited to intramuscularly, subcutaneously, intraperitoneally, intra-arterially or intravenously. The compositions can be administered alone, or can be combined with a pharmaceutically-acceptable carrier or excipient according to standard pharmaceutical practice. For the oral mode of administration, the compositions can be used in the form of tablets, capsules, lozenges, troches, powders, syrups, elixirs, aqueous solutions and suspensions, and the like. For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. For pulmonary administration, diluents and/or carriers will be selected to be appropriate to allow the formation of an aerosol. It is preferred that the conjugate of the present invention be administered parenterally, i.e. intravenously or intraperitoneally, by infusion or injection.

Preferred embodiments of the present invention are described below. It will be apparent to those of ordinary skill in the art after reading the following description that modifications and variations are possible, all of which are intended to fall within the scope of the claims.

EXAMPLE 1

Preparation of a Homogeneous Transferrin-doxorubicin Conjugate

The synthesis of large amounts of homogeneous transferrin-doxorubicin conjugates with predetermined molecular ratios was done stoichiometrically by employing the only amino group of doxorubicin (DOX), which is at the 3' amino position, to react with one of the two reactive groups on glutaraldehyde (GLU). The first step was to add GLU dropwise to DMSO in an ice cold water bath. Next was the dropwise addition of a saline solution of DOX into a saline solution of GLU+DMSO to a final concentration of a 1:1 molar ratio of DOX-to-GLU. The resulting solution of DOX-GLU was stirred three hours at room temperature in the dark.

The molarities of DOX and GLU were the same in the above reaction in order to produce a final solution of DOX-GLU that contains neither free DOX nor free GLU. However, there is the possibility of free GLU in solution if one GLU reacts with two DOX to produce DOX-GLU-DOX, but this possibility is minimized by the mass action kinetics generated by drop-wise addition of monovalent DOX into the solution of bivalent GLU. The volumes of these reactants are not restricted, so large amounts of homogeneous DOX-GLU can be prepared.

Subsequently DOX-GLU was added to transferrin (TRF) by drop-wise addition into a saline solution of the transferrin (TRF). The TRF can be either iron-free (apo-transferrin) or iron-saturated (holo-transferrin). The desired molar ratio of DOX to TRF was obtained by appropriately adjusting the volume of TRF. The resulting solution of TRF-GLU-DOX was stirred for 20 hours at room temperature in the dark. Unlike the reaction of DOX with GLU, the reaction of DOX-GLU with TRF is not restricted to one binding site, for the GLU component of DOX-GLU can react with any one of several epsilon-amino lysine groups in the TRF molecule.

The number of DOX molecules bound to TRF was determined in the second step. For example, if the starting ratio of DOX-GLU to TRF was 7.2:1.0, the final solution of TRF-GLU-DOX would have contained 2.5 molecules of DOX per molecule of TRF. However, if the starting ratio of DOX-GLU to TRF was 4.0:1.0, the final solution of TRF-GLU-DOX would have contained 1.4 molecules of DOX per molecule of TRF. Similarly, if the starting ratio of DOX-GLU to TRF was 2.5:1.0, the final solution of TRF-GLU-DOX would have contained 0.9 molecules of DOX per molecule of TRF. In this way, large amounts of TRF-GLU-DOX with predetermined ratios of DOX-to-TRF can be provided according to the need.

Any excess GLU remaining in the reaction product can be scavenged by the addition of ethanolamine, followed by centrifugation and dialysis. Although reactions with DOX and TRF theoretically consume all of the GLU, ethanolamine was added to the final reaction mixture to bind any available GLU. This reaction was allowed to continue for 30 minutes in the dark. The final solution was centrifuged at 2000 rpm for 10 minutes, dialyzed twice for 6 hours in a 100-fold excess of saline and three times in the same excess of Hepes buffered saline, and the resulting TRF-GLU-DOX conjugates were ready for use.

Biochemical Characterization of the Conjugates:

By using HPLC and polyacrylamide gel electrophoresis, the homogeneity of TRF-GLU-DOX conjugates can be determined. Also, by using spectrophotometry, the molecular ratio of DOX-to-TRF can be determined. These techniques repeatedly have revealed a consistent homogeneity of the TRF-GLU-DOX conjugates. In addition, chromatography is not required in the preparation of these conjugates, because there are no aggregates or fragments. This allows for the preparation of large volumes of homogeneous transferrin-drug conjugates, which increases yields and decreases costs.

The expenses caused by losses of TRF and DOX in other types of transferrin-drug conjugates have been an impediment to their use. For example, yields of DOX and TRF are decreased by using procedures such as thiolation that alter the drug and/or protein. Yields also are decreased by using solvent systems and by chromatography used to prepare acid-stable and acid-labile linkages. The GLU bond between DOX and TRF is acid-stable, and yields of DOX and TRF in TRF-DOX conjugates prepared according to this invention are high. Indeed, compared to other known procedures, the yield for TRF is nearly doubled (90% vs 50%), and the yield for DOX is increased 5-fold.

None of the previously known approaches to the preparation of transferrin-doxorubicin conjugates are capable of producing large amounts of homogeneous conjugates with predetermined ratios of the number of drug molecules per molecule of transferrin. In addition, the other approaches employ chromatography to eliminate aggregates and to harvest fractions that are enriched in homogeneous conjugates. These procedures decrease yields, increase costs, and lack the ability to predetermine molecular ratios.

EXAMPLE 2

Preparation of a Transferrin-apoptosis Inducing Compound (Deferoxamine) Conjugate Glutaraldehyde (GLU) is added drop-wise to DMSO in an ice cold water bath followed by the drop-wise addition of a saline solution of deferoxamine (DEF) into a saline solution of GLU+DMSO to a final concentration of a 2:1 molar ratio of DEF-to-GLU. The resulting solution of DEF-GLU is stirred three hours at room temperature in to the dark.

The DEF-GLU is added drop-wise to a saline solution of transferrin (TRF). The TRF can be either iron-free (apo-transferrin) or iron-saturated (holo-transferrin). The desired molar ratio of DEF to TRF is obtained by appropriately adjusting the volume of TRF. The resulting solution of TRF-GLU-DEF was stirred for 20 hours at room temperature in the dark. Unlike the reaction of DEF with GLU, the reaction of DEF-GLU with TRF is not restricted to one binding site, for the GLU component of DEF-GLU can react with any one of several epsilon-amino lysine groups in the TRF molecule.

The number of DEF molecules bound to TRF is determined during the addition of DEF-GLU to TRF. For example, if the starting ratio of DEF-GLU to TRF was 7.2:1.0, the final solution of TRF-GLU-DEF would have contained 2.5 molecules of DEF per molecule of TRF. However, if the starting ratio of DEF-GLU to TRF is 4.0:1.0, the final solution of TRF-GLU-DEF would have contain 1.4 molecules of DEF per molecule of TRF. Similarly, if the starting ratio of DEF-GLU to TRF is 2.5:1.0, the final solution of TRF-GLU-DEF would contain 0.9 molecules of DEF per molecule of TRF. In this way, large amounts of TRF-GLU-DEF with predetermined ratios of DEF-to-TRF can be provided according to need.

Ethanolamine is normally added to the reaction product followed by centrifugation and dialysis. Although reactions with DEF and TRF theoretically consume all of the GLU, ethanolamine is added to the final reaction mixture to bind any available GLU. This reaction is allowed to continue for 30 minutes in the dark. The final solution is centrifuged at 2000 rpm for 10 minutes, dialyzed twice for 6 hours in a 100-fold excess of saline and three times in the same excess of Hepes buffered saline, and the resulting TRF-GLU-DEF conjugates are ready for use.

REFERENCES (References in Bold Type are from Dr. Faulk's Laboratory)
1. Faulk W P, Hsi B L and Stevens P J. Transferrin and transferrin receptors in carcinoma of the breast. Lancet 1980; ii: 390-392
2. Faulk W P, Harats H and Berczi A. Transferrin receptor growth control in normal and abnormal cells. In: *Oxidoreduction at the Plasma Membrane*. Vol 1. (eds., F L Crane, J D Morre and H Low) CRC Press, Boca Raton, Fla., 1990; pp. 205-224.
3. Yang D C, Wang F, Elliott R L and Head J F. Expression of transferrin receptor and ferritin H-chain mRNA are associated with clinical and histopathological prognostic indicators in breast cancer. Anticancer Res 2001; 21: 541-549.
4. Yeh C J G, Taylor C G and Faulk W P. Targeting of cytotoxic drugs by transferrin receptors: Selective killing of acute myelogenous leukemia cells. Protides Biol Fluids 1984; 32: 441-444.

5. Barnett D, Wilson G A, Lawrence A C and Buckley G A. Transferrin receptor expression in the leukaemias and lymphoproliferative disorders. Clin Lab Haematol 1987; 9: 361-70.
6. Whitney J F, Clark J M, Griffin T W, Gautam S and Leslie K O. Transferrin receptor expression in nonsmall cell lung cancer. Histopathologic and clinical correlates. Cancer 1995; 76: 20-25.
7. Recht L, Torres C O, Smith T W, Raso V and Griffin T W. Transferrin receptor in normal and neoplastic brain tissue: implications for brain-tumor immunotherapy. J Neurosurg 1990; 72: 941-945.
8. Sciot R, Paterson A C, van Eyken P, Callea F, Kew M C and Desmet V J. Transferrin receptor expression in human hepatocellular carcinoma: an immunohistochemical study of 34 cases. Histopathol 1988; 12: 53-63
9. Seymour G J, Walsh M D, Lavin M F, Strutton G and Gardiner R A. Transferrin receptor expression by human bladder transitional cell carcinomas. Urol Res 1987;15: 341-344.
10. Lindholm M L, Lindberg L A, Vilja P, Puolakka V M, Nordling S, Schroder T and Schroder J. Expression of the human transferrin receptor in subrenal capsule assay in the mouse. J Surg Oncol 1988; 38: 57-62.
11. Hereiz H A and Bayoumi F A. Evaluation of diagnosis of ovarian malignancy using immunohistochemical technique. J Egyptian Public Hlth Assoc 1992; 67: 697-707.
12. Medeiros L J, Picker L J, Horning S J and Warnke R A. Transferrin receptor expression by non-Hodgkin's lymphomas. Correlation with morphologic grade and survival. Cancer 1988; 61: 1844-185.
13. Yeh C J G, Taylor C and Faulk W P. Transferrin binding by peripheral blood mononuclear cells in human lymphomas, myelomas and leukemias. Vox Sanguinis 1984; 46: 217-223.
14. Soyer H P, Smolle J, Torne R and Kerl H. Transferrin receptor expression in normal skin and in various cutaneous tumors. J Cutaneous Pathol 1987; 14: 1-5.
15. Pannccio M, Zalcberg J R, Thompson C H, Leyden J M, Sullivan J R, Lichtenstein M and McKenzie I F. Heterogeneity of the human transferrin receptor and use of anti-transferrin receptor antibodies to detect tumors in vivo. Immunol & Cell Biol 1987; 65: 461-472.
16. Farley J, Loup D, Nelson M, Miller M J, Taylor R and Gray K. Transferrin in normal and neoplastic endocervical tissues: distribution and receptor expression. Analyst & Quant Cytol & Histol 1998; 20: 238-249.
17. Lesley J, Hyman R, Schulte R and Trotter J. Expression of transferrin receptor on murine hematopoietic progenitors. Cell Immunol 1984; 83: 14-25.
18. Testa U, Pelosi E and Peschle C. The transferrin receptor. Crit Rev Oncogen 1993; 4: 241-276.
19. Bothwell T A, Charlton R W, Cook J D and Finch C A. *Iron Metabolism in Man*, Blackwell Scientific, Oxford, 1979.
20. Ponka P and Lok C N. The transferrin receptor: role in health and disease. Int J Biochem Cell Biol 1999; 31: 1111-1137.
21. Hamilton T A, Gray P W and Adams D O. Expression of the transferrin receptor on murine peritoneal macrophages is modulated by in vitro treatment with interferon gamma. Cell Immunol 1984; 89: 478-488.
22. Byrd T F and Horowitz M A. Interferon gamma-activated human monocytes downregulate transferrin receptors and inhibits the intracellular multiplication of *Legionella. pneumophila* by limiting the availability of iron. J Clin Invest 1989; 83: 1457-1465.
23. Kronke M, Leonard W, Depper J M and Greene W C. Sequential expression of genes involved in human T lymphocyte growth and differentiation. J Exp Med 1985; 161: 1593-1598.
24. Galbraith R M and Galbraith G M. Expression of transferrin receptors on mitogen-stimulated human peripheral blood lymphocytes: relation to cellular activation and related metabolic events. Immunology 1983; 133: 703-710.
25. Neckers L M and Cossman J. Transferrin receptor induction in mitogen-stimulated human T lymphocytes is required for DNA synthesis and cell division and is regulated by interleukin 2. Proc Nat Acad Sci USA 1983; 80: 3494-3498.
26. Testa U, Kuhn L, Petrini M, Quaranta M T, Pelosi E and Peschle C. Differential regulation of iron regulatory element-binding protein(s) in cell extracts of activated lymphocytes versus monocytes-macrophages. J Biol Chem 1991; 266: 3925-3930.
27. Seiser C, Texieira S and Kuhn L C. Interleukin-2-dependent transcriptional and post-transcriptional regulation of transferrin receptor mRNA. J Biol Chem 1993; 268: 13,074-13,080.
28. Neckers L M, Yenokida G and James S P. The role of the transferrin receptor in human B lymphocyte activation. J Immunol 1984; 133: 2437-2441.
29. Neckers L M and Trepel J B. Transferrin receptor expression and the control of cell growth. Cancer Invest 1986; 4: 461-470.
30. Yeh C J G, Papamichail M and Faulk W P. Loss of transferrin receptors following induced differentiation of HL-60 promyelocytic leukemia cells. Exper Cell Res 1982; 138: 429-431.
31. Barker K A and Newburger P E. Relationships between the cell cycle and the expression c-myc and transferrin receptor genes during induced myeloid differentiation. Exper Cell Res 1990; 186: 1-5.
32. Klausner R D, Rouault T A and Harford J B. Regulating the fate of mRNA: the control of cellular iron metabolism. Cell 1993; 72: 19-28.
33. Haile D J. Regulation of genes of iron metabolism by the iron-response proteins. Am J Med Sciences 1999; 318: 230-240.
34. Gatter K C, Brown G, Trowbridge I S, Woolston R E and Mason D Y. Transferrin receptors in human tissues: their distribution and possible clinical relevance. J Clin Pathol 1983; 36: 539-545.
35. Faulk W P and Hunt J S. Human placentae: view from an immunological bias. Am J Reprod Immunol 1990; 21: 108-113.
36. Broadwell R D, Baker-Caims B J, Friden P M, Oliver C and Villegas J C. Transcytosis of protein through the mammalian cerebral epithelium and endothelium. III. Receptor mediated transcytosis through the blood-brain barrier of blood-borne transferrin and antibody against transferrin receptor. Exp Neurol 1996; 142: 47-65.
37. Sylvester S R and Griswold M D. The testicular iron shuttle: A "nurse" function of the Sartoli cells. J Androl 1994; 15: 381-385.
38. Yeh C J G and Faulk W P. Killing of human tumor cells in culture with doxorubicin conjugates of human transferrin. Clin Immunol Immunopath 1984; 32: 1-11.
39. Berczi A, Barabas K, Sizensky J A and Faulk W P. Doxorubicin conjugates of human transferrin bind transferrin receptors and kill K562 and HL60 cells. Arch Biochem Biophys 1993; 300: 356-363.

40. Lai B T, Gao J P and Lanka K W. Mechanism of action and spectrum of cell lines sensitive to a doxorubicin-transferrin conjugate. Cancer Chemother & Pharmacol 1998; 41: 155-160.
41. Kratz F, Beyer U, Roth T, Tarasova N, Collery P, Lechenault F, Cazabat A, Schumacher P, Unger C and Falken U. Transferrin conjugates of doxorubicin: synthesis, characterization, cellular uptake, and in vitro efficacy. J Pharm Sciences 1998; 87: 338-346.
42. Tanaka T, Kaneo Y and Miyashita M. Synthesis of transferrin-mitomycin C conjugate as a receptor-mediated drug targeting system. Biol Pharm Bull 1996; 19: 774-777.
43. Sasaki K, Kohgo Y, Kato J, Kondo H and Niitsu Y. Intracellular metabolism and cytotoxicity of transferrin-neocarzinostatin conjugates of differing molar ratios. Jpn J Cancer Res 1993; 84: 191-196.
44. Laske D W, Youle R J and Oldfield E H. Tumor regression with regional distribution of the targeted toxin TF-CRM107 in patients with malignant brain tumors. Nature Med 1997; 3: 1362-1368.
45. Beyer U, Roth T, Schumacher P, Maier G, Unold A, Frahm A W, Fiebig H H, Unger C and Kratz F. Synthesis and in vitro efficacy of transferrin conjugates of the anticancer drug chlorambucil. J Med Chem 1998; 41: 2701-2708.
46. Bicamumpaka E and Page M. In vitro cytotoxicity of paclitaxel-transferrin conjugate on H69 cells. Oncol Reports 1998; 5: 1381-1383.
47. Lemieux P, Page M and Noel C. In vivo cytotoxicity and antineoplastic activity of a transferrin-daunorubicin conjugate. In Vivo 1992; 6: 621-627.
48. Guo M, Sun H, McArdle H J, Gambling L and Sadler P J. Ti(IV) uptake and release by human serum transferrin and recognition of Ti(IV)-transferrin by cancer cells: understanding the mechanism of action of the anticancer drug titanocene dichloride. Biochem 2000; 39: 10023-10033.
49. Shah D and Shen W C. Transcellular delivery of an insulin-transferrin conjugate in enterocyte-like Caco-2 cells. J Pharm Sciences 1996; 85: 1306-1311.
50. Drobyski W R, UI-Haq R, Majewski D and Chitambar C R. Modulation of in vitro and in vivo T-cell responses by transferrin-gallium and gallium nitrate. Blood 1996; 88: 3056-3064.
51. Hoshino T, Misaki M, Yamamoto M, Shimizu H, Ogawa Y and Toguchi H. In vitro cytotoxicities and in vivo distribution of transferrin-platinum(II) complex. J Pharm Sciences 1995; 84: 216-221.
52. Ippoliti R, Ginobbi P, Lendaro E, D'Agostino I, Ombres D, Benedetti P A, Brunori M and Citro G. The effect of monensin and chloroquine on the endocytosis and toxicity of chioneric toxins. Cell Mol Life Sci 1998; 54: 866-875.
53. Kratz F, Hartmann F, Keppler B and Messor L. The binding properties of two antitumor ruthenium(III) complexes to apotransferrin. J Biol Chem 1994; 269: 2581-2588.
54. Park E, Starzyk R M, McGrath J P, Lee T, George J, Schutz A J, Lynch P and Putney S D. Production and characterization of fusion proteins containing transferrin and nerve growth factor. J Drug Targeting 1998; 6: 53-64.
55. Ali S A, Joao H C, Hammerschmid F, Eder J and Steinkasserer A. Transferrin Trojan Horses as a rational approach for biological delivery of therapeutic peptide domains. J Biol Chem 1999; 274: 24066-24073.
56. Peters K and Richards F M. Chemical cross-linking: reagents and problems in studies of membrane structure. Annu Rev Biochem 1977; 46: 523-551.
57. Rhodes J. Evidence for an intercellular covalent reaction essential in antigen-specific T cell activation. J Immunol 1989; 143: 1482-1489.
58. Tritton T R. Cell surface actions of doxorubicin. Pharmacol & Therapeutics 1991: 49: 293-309.
59. Maestre N, Tritton T R, Laurent G and Jaffrezou J P. Cell surface-directed interaction of anthracyclines leads to cytotoxicity and nuclear factor kappaB activation but not apoptosis signaling. Cancer Res 2001; 61: 2558-2561.
60. Fong W F, Lam W, Yang M and Wong J T-F. Partial synergism between dextran-conjugated doxorubicin and cancer drugs on the killing of multidrug resistant KB-VI cells. Anticancer Res 1996; 16: 3773-3778.
61. Sainte-Marie J, Lafont V, Pecheur E I, Favero J, Philippot J R and Bienvenue A. Transferrin receptor functions as a signal-transduction molecule for its own recycling via increases in the internal Ca++concentration. Euro J Biochem 1997; 250: 689-697.
62. Crane F L, Low H, Sun I L, Morre D J and Faulk W P. Interaction between oxidoreductase, transferrin receptor and channels in the plasma membrane. In: *Growth Factors from Genes to Clinical Applications* (eds, V R Sara, K Hall and H Low) Raven Press, New York, 1990; pp. 228-239.
63. Sun I L, Navas P, Crane F L, Morre D J and Low H. Diferric transferrin reductase in the plasma membrane is inhibited by doxorubicin. Biochem Int 1987; 14: 119-127.
64. Faulk W P, Harats H, McIntyre J A, Berczi A, Sun I L and Crane F L. Recent advances in cancer research: Drug targeting without the use of monoclonal antibodies. Am J Reprod Immunol 1989; 21: 151-154.
65. Morre D J, Kim C, Paulik M, Morre D M and Faulk W P. Is the drug-response NADH-oxidase of the cancer cell plasma membrane a molecular target for doxorubicin? Bioenerg Biomembr 1997; 29: 269-280.
66. Sun I L, Sun E E, Crane F L, Morre D J and Faulk W P. Inhibition of transplasma membrane electron transport by transferrin-doxorubicin conjugates. Biochim Biophy Acta 1992; 1105: 84-88.
67. Faulk W P, Barabas K, Sun I L and Crane F L. Transferrin-doxorubicin conjugates which inhibit tumor cell proliferation without interaction with DNA inhibit plasma membrane oxidoreductase and proton release in K562 cells. Biochem Int 1991; 25: 815-822.
68. Hileti D, Panayiotidis P and Hoffbrand V. Iron chelators induce apoptosis in proliferating cells. Brit J Haematol 1995; 89: 181-187.
69. Leardi A, Caraglia M, Selleri C, Pepe S, Pizzi C, Notaro R, Fabbrocini A, De Lorenzo S, Musico M, Abbruzzese A, Bianco A and Tagliaferri P. Desferioxamine increases iron depletion and apoptosis induced by ara-C of human myeloid leukemic cells. Brit J Haematol 1998; 102: 746-752.
70. Barabas K, Miller S J and Faulk W P. Regulation of transferrin receptor mRNA stability in drug-sensitive and drug-resistant cancer cells. To be submitted for publication, 2001.
71. Hentze M W and Kuhn L C. Molecular control of vertebrate iron-metabolism: mRNA-based regulatory circuits operated by iron, nitric oxide and oxidative stress. Proc Natl Acad Sci USA 1996; 93: 8175-8182.
72. Pantapoulos K and Hentze M W. Rapid responses to oxidative stress mediated by iron regulatory protein. EMBO J. 1995; 14: 2917-1924.
73. Richardson D R, Naumannova V, Nagy E and Ponka P. The effect of redox-related species of nitrogen monoxide on transferrin and iron uptake and cellular proliferation of erythroleukemia (K562) cells. Blood 1995; 86: 3211-3219.

74. Laske D W, Ilercil O, Akbasak A, Youle R J and Oldfield E H. Efficacy of direct intratumoral therapy with targeted protein toxins for solid human gliomas in nude mice. J Neurosurg 1994; 80: 520-526.
75. Singh M, Atwal H and Micetich R. Transferrin directed delivery of doxorubicin to human cells. Anticancer Res 1998; 18(3A): 1423-1427.
76. Sato Y, Yamauchi N, Takahashi M, Sasaki K, Fukaura J, Neda H, Fujii S, Hirayma M, Itoh Y, Koshita Y, Kogawa K, Kato J, Sakamaki S and Niitsu Y. In vivo gene delivery to tumor cells by transferrin-streptavidin-DNA conjugate. FASEB Journal 2000; 14: 2108-2118.
77. Faulk W P, Taylor C G, Yeh G and McIntyre J A. Preliminary clinical study of transferrin-doxorubicin conjugate for drug delivery to acute leukemia patients. Mol Biother 1990; 2: 57-60.
78. Laske D W, Morrison P F, Lieberman D M, Carthesy M E, Reynolds J C, Stewart-Henney P A, Koong S S, Cummins A, Paik C H and Oldfield E H. Chronic interstitial infusion of protein to primate brain: determination of drug distribution and clearance with single-photon emission computerized tomography imaging. J Neurosurg 1997; 87: 586-594.
79. Marbeuf-Gueye C, Ettori D, Priebe W, Kozlowski H and Garnier-Suillerot A. Correlation between the kinetics of anthracycline uptake and the resistance factor in cancer cells expressing the multidrug resistance protein or the P-glycoprotein. Biochem Biophy Acta 1999; 1450: 374-384.
80. Klausner R D, vanReuswoude J, Ashwell G, Kempf C, Schechter A N, Dean A and Bridges K. Receptor-mediated endocytosis of transferrin in K562 cells. J Biol Chem 1983; 258: 4715-4724.
81. Berczi A, Ruthner M, Szuts V, Fritzer M, Schweinzer E and Goldenberg H. Influence of conjugation of doxorubicin to transferrin on the iron uptake by K562 cells via receptor-mediated endocytosis. Euro J Biochem 1993; 213: 427-436.
82. Fritzer M, Barabas K, Szuts V, Berczi A, Szekeres T, Faulk W P and Goldenberg H. Cytotoxicity of a transferrin-doxorubicin conjugate to anthracylcine resistant cells. Int J Cancer 1992; 52: 619-623.
83. Hatano T, Ohkawa K and Matsuda M. Cytotoxic effect of the protein-doxorubicin conjugates on the multidrug-resistant human myelogenous leukemia cell line, K562, in vitro. Tumor Biology 1993; 14: 288-294.
84. Lemieux P and Page M. Sensitivity of multidrug-resistant MCF-7 cells to a transferrin-doxorubicin conjugate. Anticancer Res 1994; 14(2A): 397-403.
85. Fritzer M, Szekeres T, Szuts V, Jraayam H N and Goldenberg H. Cytotoxic effects of a doxorubicin-transferrin conjugate in multidrug-resistant KB cells. Biochem Pharm 1996; 51: 489-493.
86. Wang F, Jiang X, Yang D C, Elliot R L and Head J F. Doxorubicin-gallium-transferrin conjugate overcomes multidrug resistance: evidence for drug accumulation in the nucleus of drug resistant MCF-7/ADR cells. Anticancer Res 2000; 20: 799-808.
87. Soma C E, Dubernet C and Barratt G. Ability of doxorubicin-loaded nanoparticles to overcome multidrug resistance of tumor cells after their capture by macrophages. Pharm Res 1999; 16: 1710-1716.
88. Mazel M, Clair P, Rousselle C, Vidal P, Scherrmann J-M, Mathieu D and Temsamani J. Doxorubicin-peptide conjugates overcome multidrug resistance. Anti-Cancer Drugs 2001; 12: 107-116.
89. Barabas K, Sizensky J A and Faulk W P. Transferrin conjugates of doxorubicin are cytotoxic without intercalating nuclear DNA. J Biol Chem 1992; 267: 9437-9442.
90. Barabas K and Faulk W P. Transferrin receptors associate with drug resistance in cancer cells. Biochem Biophys Res Com 1993; 197: 702-708.

The invention claimed is:

1. A method for selectively treating a tumor by iron restriction therapy, comprising administering to a patient with a tumor an anti-tumor effective amount of a substantially homogeneous conjugate comprising a targeting agent and a bioaffecting material, wherein said bioaffecting material is an apoptosis inducing compound and said targeting agent is selected from the group consisting of transferrin, somatostatin, epidermal growth factor, folic acid and transcobalamin, and wherein said homogeneous conjugate is substantially free of dimers, trimers and aggregates, wherein said apoptosis inducing compound restricts iron.

2. The method according to claim 1, further comprising administering free iron or transferrin bound iron to said patient.

3. The method according to claim 1, wherein said apoptosis inducing compound which restricts iron is deferoxamine.

4. A method for selectively treating target cells, comprising contacting target cells with a substantially homogeneous conjugate comprising a targeting agent and a bioaffecting material, wherein said bioaffecting material is an apoptosis inducing compound and said targeting agent is selected from the group consisting of transferrin, somatostatin, epidermal growth factor, folic acid and transcobalamin, and wherein said homogeneous conjugate is substantially free of dimers, trimers and aggregates, and administering free iron or transferrin bound iron to said target cells.

* * * * *